United States Patent
Murphy et al.

(10) Patent No.: US 8,911,515 B2
(45) Date of Patent: *Dec. 16, 2014

(54) CANDLE AND CANDLE WAX CONTAINING METATHESIS AND METATHESIS-LIKE PRODUCTS

(71) Applicant: Elevance Renewable Sciences, Inc., Woodridge, IL (US)

(72) Inventors: Timothy A. Murphy, Yorkville, IL (US); Michael J. Tupy, Crystal, MN (US); Timothy W. Abraham, Minnetonka, MN (US); Andy Shafer, Minnetonka, MN (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/167,767

(22) Filed: Jan. 29, 2014

(65) Prior Publication Data

US 2014/0144069 A1    May 29, 2014

Related U.S. Application Data

(63) Continuation of application No. 11/795,052, filed as application No. PCT/US2006/000822 on Jan. 10, 2006, now Pat. No. 8,685,118.

(60) Provisional application No. 60/642,600, filed on Jan. 10, 2005, provisional application No. 60/690,122, filed on Jun. 13, 2005.

(51) Int. Cl.
| | |
|---|---|
| *C10L 1/18* | (2006.01) |
| *A61K 9/02* | (2006.01) |
| *C11C 5/00* | (2006.01) |
| *C11C 3/12* | (2006.01) |
| *C11C 3/00* | (2006.01) |
| *C08L 91/06* | (2006.01) |
| *A61L 9/02* | (2006.01) |

(52) U.S. Cl.
CPC . *C11C 5/002* (2013.01); *C11C 3/12* (2013.01); *C11C 3/00* (2013.01); *C08L 91/06* (2013.01); *A61L 9/02* (2013.01)
USPC ............ 44/308; 44/275; 44/288; 424/401

(58) Field of Classification Search
USPC .................. 431/288–297; 508/450–451; 44/288–297, 275, 588, 308; 424/401
See application file for complete search history.

(56) References Cited

U.S. PATENT DOCUMENTS

| | | | |
|---|---|---|---|
| 1,935,946 A | 11/1933 | Egan et al. | |
| 1,954,659 A | 4/1934 | Will | |

(Continued)

FOREIGN PATENT DOCUMENTS

| | | |
|---|---|---|
| DE | 19956226 | 5/2001 |
| EP | 0 429 995 A2 | 6/1991 |

(Continued)

OTHER PUBLICATIONS

Anderson et al., "Synthesis and Reactivity of Olefin Metathesis Catalysts Bearing Cyclic (Alkyl)(Amino) Carbenes," Angewandte Chemie International Edition, vol. 46, 2007, pp. 7262-7265.

(Continued)

*Primary Examiner* — Pamela H Weiss
(74) *Attorney, Agent, or Firm* — Brinks Gilson & Lione

(57) ABSTRACT

A wax comprises a metathesis product and/or a product that resembles, at least in part, a product which may be formed from a metathesis reaction. The wax may be used to form articles for example, candles (container candles, votive candles, and/or a pillar candles), crayons, fire logs or tarts. The wax commonly includes other components in addition to the metathesis product.

20 Claims, 3 Drawing Sheets

Trimer

(56) References Cited

U.S. PATENT DOCUMENTS

| | | |
|---|---|---|
| 2,294,229 A | 8/1942 | Fiero |
| 2,468,799 A | 5/1949 | Ziels et al. |
| 2,619,422 A | 11/1952 | Whiting |
| 2,784,891 A | 3/1957 | Thielke |
| 3,448,178 A | 6/1969 | Flanagan |
| 3,630,697 A | 12/1971 | Duling et al. |
| 3,645,705 A | 2/1972 | Miller et al. |
| 3,744,956 A | 7/1973 | Hess |
| 3,844,706 A | 10/1974 | Tsaras |
| 3,896,053 A | 7/1975 | Broecker et al. |
| 4,118,203 A | 10/1978 | Beardmore et al. |
| 4,134,718 A | 1/1979 | Kayfetz et al. |
| 4,292,088 A | 9/1981 | Scheuffgen et al. |
| 4,293,345 A | 10/1981 | Zeilstra et al. |
| 4,314,915 A | 2/1982 | Wiegers et al. |
| 4,390,590 A | 6/1983 | Saunders et al. |
| 4,411,829 A | 10/1983 | Schulte-Elte et al. |
| 4,434,306 A | 2/1984 | Kobayashi et al. |
| 4,507,077 A | 3/1985 | Sapper |
| 4,545,941 A | 10/1985 | Rosenburg |
| 4,554,107 A | 11/1985 | Takao |
| 4,567,548 A | 1/1986 | Schneeberger |
| 4,608,011 A | 8/1986 | Comstock |
| 4,614,625 A | 9/1986 | Wilson |
| 4,623,488 A | 11/1986 | Takao |
| 4,634,606 A | 1/1987 | Skogg |
| 4,714,496 A | 12/1987 | Luken, Jr. et al. |
| 4,759,709 A | 7/1988 | Luken, Jr. et al. |
| 4,813,975 A | 3/1989 | Poulina et al. |
| 4,842,648 A | 6/1989 | Phadoemchit et al. |
| 4,855,098 A | 8/1989 | Taylor |
| 4,923,708 A | 5/1990 | Given, Jr. |
| 5,043,485 A | 8/1991 | Fleckenstein et al. |
| 5,142,072 A | 8/1992 | Stipp et al. |
| 5,171,329 A | 12/1992 | Lin |
| 5,258,197 A | 11/1993 | Wheeler et al. |
| 5,338,187 A | 8/1994 | Elharar |
| 5,380,544 A | 1/1995 | Klemann et al. |
| 5,506,363 A | 4/1996 | Grate et al. |
| 5,578,089 A | 11/1996 | Elsamaloty |
| 5,639,526 A | 6/1997 | Kotsiopoulos et al. |
| 5,660,865 A | 8/1997 | Pedersen et al. |
| 5,700,516 A | 12/1997 | Sandvick et al. |
| 5,723,137 A | 3/1998 | Wahle et al. |
| 5,734,070 A | 3/1998 | Tacke et al. |
| 5,753,015 A | 5/1998 | Sinwald et al. |
| 5,843,194 A | 12/1998 | Spaulding |
| 5,885,600 A | 3/1999 | Blum et al. |
| 5,888,487 A | 3/1999 | Baumoeller et al. |
| 6,001,286 A | 12/1999 | Sleeter |
| 6,019,804 A | 2/2000 | Requejo et al. |
| 6,022,402 A | 2/2000 | Stephenson et al. |
| 6,063,144 A | 5/2000 | Calzada et al. |
| 6,099,877 A | 8/2000 | Schuppan |
| 6,103,308 A | 8/2000 | Floyd et al. |
| 6,106,597 A | 8/2000 | Starks et al. |
| 6,123,979 A | 9/2000 | Hepburn et al. |
| 6,127,326 A | 10/2000 | Dieckmann et al. |
| 6,132,742 A | 10/2000 | Le Bras et al. |
| 6,156,369 A | 12/2000 | Eger et al. |
| 6,169,198 B1 | 1/2001 | Fischer et al. |
| 6,197,894 B1 | 3/2001 | Sunaga et al. |
| 6,201,053 B1 | 3/2001 | Dieckmann et al. |
| 6,211,315 B1 | 4/2001 | Larock et al. |
| 6,214,918 B1 | 4/2001 | Johnson et al. |
| 6,224,641 B1 | 5/2001 | Matzat et al. |
| 6,238,926 B1 | 5/2001 | Liu et al. |
| 6,255,375 B1 | 7/2001 | Michelman |
| 6,258,965 B1 | 7/2001 | O'Lenick, Jr. |
| 6,262,153 B1 | 7/2001 | Webster et al. |
| 6,276,925 B1 | 8/2001 | Varga |
| 6,277,310 B1 | 8/2001 | Sleeter |
| 6,281,163 B1 | 8/2001 | Van Dijk |
| 6,284,007 B1 | 9/2001 | Tao |
| 6,486,264 B1 | 11/2002 | Tsunogae et al. |
| 6,497,735 B2 | 12/2002 | Tao |
| 6,503,077 B2 | 1/2003 | Orth et al. |
| 6,503,285 B1 | 1/2003 | Murphy |
| 6,582,748 B1 | 6/2003 | Loh et al. |
| 6,586,506 B2 | 7/2003 | Webster et al. |
| 6,599,334 B1 | 7/2003 | Anderson |
| 6,645,261 B2 | 11/2003 | Murphy et al. |
| 6,673,763 B1 | 1/2004 | Hansen et al. |
| 6,696,597 B2 | 2/2004 | Pederson et al. |
| 6,716,155 B2 | 4/2004 | Sleeter |
| 6,730,137 B2 | 5/2004 | Pesu et al. |
| 6,733,548 B2 | 5/2004 | Rasmussen et al. |
| 6,758,869 B2 | 7/2004 | Roeske et al. |
| 6,770,104 B2 | 8/2004 | Murphy |
| 6,773,469 B2 | 8/2004 | Murphy |
| 6,797,020 B2 | 9/2004 | Murphy |
| 6,824,572 B2 | 11/2004 | Murphy |
| 6,846,573 B2 | 1/2005 | Seydel |
| 6,852,140 B1 | 2/2005 | Roeske |
| 6,900,347 B2 | 5/2005 | Paulson et al. |
| 6,943,262 B2 | 9/2005 | Kodali et al. |
| 6,962,729 B2 | 11/2005 | Tokas et al. |
| 6,987,154 B2 | 1/2006 | Choi et al. |
| 7,026,495 B1 | 4/2006 | Pederson et al. |
| 7,037,439 B2 | 5/2006 | Tavares |
| 7,119,216 B2 | 10/2006 | Newman et al. |
| 7,128,766 B2 | 10/2006 | Murphy et al. |
| 7,176,171 B2 | 2/2007 | Nieendick et al. |
| 7,176,336 B2 | 2/2007 | Maughon et al. |
| 7,192,457 B2 | 3/2007 | Murphy et al. |
| 7,217,301 B2 | 5/2007 | Murphy et al. |
| 7,314,904 B2 | 1/2008 | Nadolsky et al. |
| 7,365,140 B2 | 4/2008 | Piers et al. |
| 7,387,649 B2 | 6/2008 | Tao |
| 7,462,205 B2 | 12/2008 | Murphy |
| 7,510,584 B2 | 3/2009 | Cap |
| 7,569,084 B2 | 8/2009 | Tao et al. |
| 7,576,227 B2 | 8/2009 | Lysenko |
| 7,585,990 B2 | 9/2009 | van Toor et al. |
| 7,588,607 B1 | 9/2009 | Cap |
| 7,601,184 B2 | 10/2009 | Tischendorf |
| 7,629,479 B2 | 12/2009 | Kondo et al. |
| 7,637,968 B2 | 12/2009 | Murphy |
| 7,678,932 B2 | 3/2010 | Thurier et al. |
| 7,812,185 B2 | 10/2010 | Burdett et al. |
| 7,833,294 B2 | 11/2010 | Murphy et al. |
| 8,070,833 B2 * | 12/2011 | Murphy ..................... 44/275 |
| 8,157,873 B2 * | 4/2012 | Murphy et al. ............. 44/275 |
| 8,334,052 B2 * | 12/2012 | Gruber et al. ............ 428/411.1 |
| 8,500,826 B2 * | 8/2013 | DiMaio et al. .............. 44/275 |
| 8,551,194 B2 * | 10/2013 | Uptain et al. ............... 44/275 |
| 8,652,221 B2 * | 2/2014 | Uptain et al. ............... 44/275 |
| 2001/0013195 A1 | 8/2001 | Tao |
| 2001/0051680 A1 | 12/2001 | Webster et al. |
| 2002/0005007 A1 | 1/2002 | Roeske et al. |
| 2002/0095007 A1 | 7/2002 | Larock et al. |
| 2002/0144455 A1 | 10/2002 | Bertrand et al. |
| 2002/0157303 A1 | 10/2002 | Murphy et al. |
| 2003/0008257 A1 | 1/2003 | Tao |
| 2003/0017431 A1 | 1/2003 | Murphy |
| 2003/0022121 A1 | 1/2003 | Biggs |
| 2003/0046860 A1 | 3/2003 | Tiffany et al. |
| 2003/0057599 A1 | 3/2003 | Murphy et al. |
| 2003/0061760 A1 | 4/2003 | Tao et al. |
| 2003/0091949 A1 | 5/2003 | Pesu et al. |
| 2003/0110683 A1 | 6/2003 | Murphy |
| 2003/0134244 A1 | 7/2003 | Gray et al. |
| 2003/0198826 A1 | 10/2003 | Seydel |
| 2003/0207971 A1 | 11/2003 | Stuart, Jr. et al. |
| 2003/0213163 A1 | 11/2003 | Berger et al. |
| 2003/0236377 A1 | 12/2003 | Choi et al. |
| 2004/0000088 A1 | 1/2004 | Wesley |
| 2004/0037859 A1 | 2/2004 | Cecchi et al. |
| 2004/0047886 A1 | 3/2004 | Murphy et al. |
| 2004/0076732 A1 | 4/2004 | Valix |
| 2004/0088907 A1 | 5/2004 | Murphy |
| 2004/0088908 A1 | 5/2004 | Murphy |
| 2004/0138359 A1 | 7/2004 | Dinkelaker et al. |
| 2004/0200136 A1 | 10/2004 | Tao et al. |

(56) References Cited

U.S. PATENT DOCUMENTS

| | | |
|---|---|---|
| 2004/0221503 A1* | 11/2004 | Murphy et al. ............ 44/275 |
| 2004/0221504 A1 | 11/2004 | Murphy |
| 2004/0250464 A1 | 12/2004 | Rasmussen et al. |
| 2005/0014664 A1 | 1/2005 | Nadolsky et al. |
| 2005/0027136 A1 | 2/2005 | Toor et al. |
| 2005/0060927 A1 | 3/2005 | Murphy |
| 2005/0070750 A1 | 3/2005 | Newman et al. |
| 2005/0080301 A1 | 4/2005 | Maughon et al. |
| 2005/0095545 A1 | 5/2005 | Tischendorf |
| 2005/0123780 A1 | 6/2005 | Seydel |
| 2005/0154221 A1 | 7/2005 | Lysenko et al. |
| 2005/0158679 A1 | 7/2005 | Chen et al. |
| 2005/0269728 A1 | 12/2005 | Roos |
| 2006/0079704 A1 | 4/2006 | Lacombe et al. |
| 2006/0128912 A1 | 6/2006 | Piers et al. |
| 2006/0236593 A1 | 10/2006 | Cap |
| 2006/0272199 A1 | 12/2006 | Licciardello et al. |
| 2006/0272200 A1 | 12/2006 | Murphy et al. |
| 2006/0289138 A1 | 12/2006 | Borsinger et al. |
| 2007/0006521 A1 | 1/2007 | Licciardello et al. |
| 2007/0006522 A1 | 1/2007 | Tao |
| 2007/0039237 A1 | 2/2007 | Murphy et al. |
| 2007/0056211 A1 | 3/2007 | Li et al. |
| 2007/0144058 A1 | 6/2007 | Chen et al. |
| 2007/0151480 A1 | 7/2007 | Bloom et al. |
| 2007/0179307 A1 | 8/2007 | Olivier-Bourbigou et al. |
| 2007/0270621 A1 | 11/2007 | Millis et al. |
| 2007/0282000 A1 | 12/2007 | Murphy et al. |
| 2008/0027194 A1 | 1/2008 | Schrodi |
| 2008/0064891 A1 | 3/2008 | Lee |
| 2008/0138753 A1 | 6/2008 | Tao et al. |
| 2008/0145808 A1 | 6/2008 | Lee |
| 2008/0206411 A1 | 8/2008 | Nielsen |
| 2008/0307696 A1 | 12/2008 | Wu et al. |
| 2009/0048459 A1 | 2/2009 | Tupy et al. |
| 2009/0119977 A1 | 5/2009 | Murphy |
| 2009/0126602 A1 | 5/2009 | Murphy et al. |
| 2009/0220443 A1 | 9/2009 | Braksmayer et al. |
| 2009/0259065 A1 | 10/2009 | Abraham et al. |
| 2009/0264672 A1 | 10/2009 | Abraham et al. |
| 2010/0024281 A1 | 2/2010 | Lemke et al. |
| 2010/0044924 A1 | 2/2010 | Cap |
| 2010/0047499 A1 | 2/2010 | Braksmayer et al. |
| 2010/0094034 A1 | 4/2010 | Kaido et al. |
| 2010/0132250 A1 | 6/2010 | Uptain et al. |
| 2010/0145086 A1 | 6/2010 | Schrodi et al. |
| 2010/0205851 A1 | 8/2010 | Uptain et al. |

FOREIGN PATENT DOCUMENTS

| | | |
|---|---|---|
| EP | 0 536 861 A1 | 4/1993 |
| EP | 0 545 715 A1 | 6/1993 |
| EP | 0 685 554 A1 | 12/1995 |
| EP | 0 811 664 A1 | 12/1997 |
| EP | 1 408 064 A1 | 4/2004 |
| EP | 1 693 436 A1 | 8/2006 |
| EP | 1 696 022 A1 | 8/2006 |
| EP | 1 801 096 A1 | 6/2007 |
| FR | 2878246 A1 | 5/2006 |
| JP | 56-032550 A | 4/1981 |
| JP | 56-077243 A | 6/1981 |
| JP | 04-059897 A | 2/1992 |
| JP | 06-009987 A | 1/1994 |
| JP | 09-014574 A | 1/1997 |
| SU | 1565872 | 5/1990 |
| WO | WO 92/00269 A1 | 1/1992 |
| WO | WO 94/23836 A1 | 10/1994 |
| WO | WO 96/00815 A1 | 1/1996 |
| WO | WO 96/04289 A1 | 2/1996 |
| WO | WO 96/14373 A1 | 5/1996 |
| WO | WO 98/45390 A1 | 10/1998 |
| WO | WO 99/27043 A1 | 6/1999 |
| WO | WO 00/46565 A2 | 8/2000 |
| WO | WO 01/36368 A2 | 5/2001 |
| WO | WO 02/30386 A1 | 4/2002 |
| WO | WO 02/092736 A1 | 11/2002 |
| WO | WO 03/012016 A1 | 2/2003 |
| WO | WO 03/018905 A1 | 3/2003 |
| WO | WO 03/051134 A2 | 6/2003 |
| WO | WO 03/057983 A1 | 7/2003 |
| WO | WO 03/093215 A1 | 11/2003 |
| WO | WO 03/104348 A1 | 12/2003 |
| WO | WO 2004/033388 A1 | 4/2004 |
| WO | WO 2004/062763 A2 | 7/2004 |
| WO | WO 2004/083310 A1 | 9/2004 |
| WO | WO 2004/101720 A1 | 11/2004 |
| WO | WO 2005/026106 A1 | 3/2005 |
| WO | WO 2005/042655 A2 | 5/2005 |
| WO | WO 2005/080455 A1 | 9/2005 |
| WO | WO 2006/041011 A1 | 4/2006 |
| WO | WO 2006/052688 A2 | 5/2006 |
| WO | WO 2006/076364 A2 | 7/2006 |
| WO | WO 2007/002999 A1 | 1/2007 |
| WO | WO 2007/081987 A2 | 7/2007 |
| WO | WO 2007/103398 A1 | 9/2007 |
| WO | WO 2007/103460 A2 | 9/2007 |
| WO | WO 2008/008420 A1 | 1/2008 |
| WO | WO 2008/010961 A2 | 1/2008 |
| WO | WO 2008/048520 A2 | 4/2008 |
| WO | WO 2008/063322 A2 | 5/2008 |
| WO | WO 2008/103289 A1 | 8/2008 |
| WO | WO 2008/140468 A2 | 11/2008 |
| WO | WO 2008/151064 A1 | 12/2008 |
| WO | WO 2008/157436 A1 | 12/2008 |

OTHER PUBLICATIONS

Baumann et al., "Natural Fats and Oils—Renewable Raw Materials for the Chemical Industry," Angewandte Chemie International Edition in English, vol. 27, 1988, pp. 41-62.

Behren et al., "Beeswax and other Non-Paraffin Waxes," Presented at NCA Technical Meeting, Jun. 19-20, 1991, 6 pages.

Bell et al., "Sperm Oil Replacements: Synthetic Wax Esters from Selectively Hydrogenated Soybean and Linseed Oils," Journal of the American Chemical Society, Jun. 1997, vol. 54, pp. 259-263.

Biermann et al., "New Syntheses with Oils and Fats as Renewable Raw Materials for the Chemical Industry,", Angewandte Chemie International Edition, vol. 39, 2000, pp. 2206-2224.

Boelhouwer et al., "Metathesis Reactions of Fatty Acid Esters," Progress of Lipid Research, Pergamon Press, vol. 24, No. 3, 1985, pp. 243-267.

Chatterjee et al., "Synthesis of Trisubstituted Alkenes via Olefin Cross-Metathesis," Organic Letters, vol. 1, No. 11, 1999, pp. 1751-1753.

Choi et al., "Olefin Metathesis Involving Ruthenium Enoic Carbene Complexes," Journal of the American Chemical Society, vol. 123, No. 42, 2001, pp. 10417-10418.

Connon et al., "A Solid-Supported Phosphine-Free Ruthenium Alkylidene for Olefin Metathesis in Methanol and Water," Bioorganic & Medical Chem Letters, vol. 12, No. 14, 2002, pp. 1873-1876.

Delaude et al., Metathesis, Kirk-Othmer Encyclopedia of Chemical Technology, Dec. 2005, vol. 26, pp. 920-958.

Dunne et al., "A Highly Efficient Olefin Metathesis Initiator: Improved Synthesis and Reactivity Studies," Tetrahedron Letters, vol. 44, No. 13, 2003, pp. 2733-2736.

Erhan et al., "Drying Properties of Metathesized Soybean Oil," Journal of American Oil Chemists' Society, AOCS Press, vol. 74, No. 6, 1997, pp. 703-706.

Feuge et al., "1,3-Diolein and 1,3-Distearin Esters of Fumaric, Succinic and Adipic Acids," Journal of American Chemical Society, vol. 80, 1958, pp. 6338-6341.

Frahm, "Harvest Lights: The only soy-based candle, a bright idea," available at http://www.extension.uiuc.edu/~stratsoy/new/news/html/909166253,html, Oct. 23, 1998, 2 pages.

Lavallo, "Stable Cyclic (Alkyl)(Amino) Carbenes as Rigid or Flexible, Bulky, Electron-Rich Ligands for Transition-Metal Catalysts: A Quaternary Carbon Atom Makes the Difference," Angewandte Chemie Int. Ed., vol. 44, 2005, pp. 5705-5709.

(56) References Cited

OTHER PUBLICATIONS

Maynard et al., "Purification Technique for the Removal of Ruthenium from Olefin Metathesis Reaction Products," Tetrahedron Letters, vol. 40, No. 22, 1999, pp. 4137-4140.
McNaught, A.D. and Wilkinson, A., "IUPAC. Compendium of Chemical Terminology," $2^{nd}$ Ed. (the "Gold Book"). Blackwell Scientific Publications, Oxfor (1997). XML on-line corrected version: http://goldbook.iupac.org (2006), created by Nic, M., Jirat, J., Kosata, B.; updated compiled by Jenkins, A. ISBN 0-9678550-9-8, doi: 10.1351/goldbook.L, 1 page.
Mol, "Applications of Olefin Metathesis in Oleochemistry: An Example of Green Chemistry," Green Chemistry, Royal Society of Chemistry, Cambridge, GB, vol. 4, 2002, pp. 5-13.
Mol et al., "Metathesis in Oleochemistry," J Braz Chem Soc, vol. 9, No. 1, 1998, pp. 1-11.
Mol, "Catalytic Metathesis of Unsaturated Fatty Acid Esters and Oils," Topics in Catalysis, vol. 27, No. 1-4, 2004, pp. 97-104.
Ngo et al., Methathesis of Unsaturated Fatty Acids: Synthesis of Long-Chain Unsaturated-[alpha],[omega]-Dicarboxylic Acids, Journal of the American Oil Chemists, Jul. 2006, vol. 83m Iss, 7, p. 629, 9 pgs.
Noller, Chemistry of Organic Compounds, W.B. Saunders Company, 2nd Ed., 1957, pp. 181 and 192.
Oliefabrik et al., "Paper coating", Research Disclosure Journal, Dec. 1996, 2 pages.
Orso, "New Use for Soybeans Has Bright Future," available at http://www.unitedsoybean.com/news/nr981014.htm, Oct. 14, 1998, 2 pages.
Patel et al., "High conversion and productive catalyst turnovers in cross-metathesis reactions of natural oils with 2-butene", *Green Chemistry*, 2006, vol. 8, pp. 450-454.
Refvik et al., "Ruthenium-Catalyzed Metathesis of Vegetable Oils," Journal of American Oil Chemists' Society, AOCS Press, vol. 76, No. 1, 1999, pp. 93-98.
Refvik, M.D. et al., "The Chemistry of Metathesized Soybean Oil," JAOCS, vol. 76, No. 1, 1999, pp. 99-102.
Rezaei, "Hydrogenated Vegetable Oils as Candle Wax," J. of the Am. Oil Chemists' Society, vol. 12, No. 79, Dec. 2002, pp. 1241-1247.
Schneider et al., "Synthesis of Highly Substituted Cyclopentane and Tetrahydrofuran Derivatives by Crossed Olefin Metathesis," Angewandte Chemi International Edition, vol. 35, No. 4, 1996, pp. 411-412.
Shorland, "Glycol Esters of Dibasic Acids. The Di-β-hydroxyethyl Esters," Journal of American Chemical Society, vol. 57, No. 1, 1935, pp. 115-116.
Tao, "Development of Vegetable Lipid-based Candles," available at http://abe.www.ecn.purdue.edu/ABE/Research/research94/REPORT.94.Book_68.htmls, 1994, 2 pages.
Tian, Qiingping et al., "Model Studies and the ADMET Polymerization of Soybean Oil," Journal of American Oil Chemists' Society, AOCS Press, vol. 79, No. 5, 2002, pp. 479-488.
Ward et al., "New Fat Products: Glyceride Esters of Adipic Acid," Journal of the Amiercan Oil Chemists' Society, vol. 36, 1959, pp. 667-671.
In Business, "America's Shining Example of Sustainable Business," available at http://www.candleworks.org, Mar./Apr. 1998, 3 pages.
Pages from Bitter Creek Candle Supply, Inc., website (http://www.execpc.com/~bcsupply) now at http://www.candlesupply.com, available at least by Jun. 29, 2000, 9 pages.
Pages from Ecowax, Nature's Gift, Inc., website (http://nglwax.com/ecowax.htm), available at least by Jul. 5, 2000, 3 pages.
Pages from Heartland Candleworks website, available at www.candleworks.org, available at least by Feb. 11, 2000, 4 pages.
Purdue Agriculture News, Purdue May Agriculture & Natural Resources Package, available at http://purduenews.uns.purdue.edu/UNS/paks/agpak.digest.9605.html, May 1996, 3 pages.
Purdue News, "Purdue students put the 'happy' back into birthday candles," available at http://www.purdue.edu/UNS/html4ever/9604.Schweitzer.candles.html, May 1996, 2 pages.
Purdue University School of Agriculture, 1998 Farm Progress Show, available at http://www.admin.ces.purdue.edu/anr/98fps/fpspix/930.html, 1998, 4 pages.
International Search Report and Written Opinion of the International Searching Authority for International Application No. PCT/US2006/000822, dated Jul. 14, 2006, 13 pages.
International Search Report for International Application No. PCT/US2007/015905, dated Apr. 23, 2008, 3 pages.
International Search Report and Written Opinion of the International Searching Authority for International Application No. PCT/US2007/00610, dated Oct. 11, 2007, 8 pages.
International Search Report and Written Opinion of the International Searching Authority for International Application No. PCT/US2007/005736, dated Aug. 8, 2007, 11 pages.
International Search Report and Written Opinion of the International Searching Authority for International Application No. PCT/US2007/005868, dated Nov. 9, 2007, 7 pages.
International Search Report for International Application No. PCT/US2007/015866, dated Nov. 26, 2007, 3 pages.
International Search Report for International Application No. PCT/US2007/016010, dated Mar. 11, 2008, 4 pages.
International Search Report for International Application No. PCT/US2007/021931, dated Apr. 11, 2008, 3 pages.
International Search Report for International Application No. PCT/US2007/021934, dated Jun. 17, 2008, 3 pages.
International Search Report for International Application No. PCT/US2007/021939, dated Feb. 18, 2008, 2 pages.
International Search Report and Written Opinion of the International Searching Authority for International Application No. PCT/US2008/009604, dated Oct. 27, 2008, 6 pages.
International Search Report and Written Opinion of the International Searching Authority for International Application No. PCT/US2008/009635, dated Oct. 27, 2008, 7 pages.
International Search Report for International Application No. PCT/US2008/065395, dated Sep. 29, 2008, 1 page.
International Search Report for International Application No. PCT/US2008/067025, dated Sep. 8, 2008, 1 page.
Office Action in corresponding Chinese Application No. 200680005586.4, dated Sep. 18, 2009, 3 pages.
European Search Report from counterpart European Application No. 08725649.1, dated Mar. 1, 2010, 3 pages.
Substantive Examination Adverse Report from counterpart Malaysian Application No. PI20060118, dated Nov. 13, 2009, 3 pages.
Examination Report for European Application No. 06733666.9, dated Jun. 24, 2008, 3 pages.
Response to Examination Report for European Application No. 06733666.9, dated Nov. 4, 2008, 13 pages.
Examination Report for European Application No. 06733666.9, dated Mar. 2, 2010, 5 pages.
Response to Examination Report for European Application No. 06733666.9, dated Sep. 13, 2010, 8 pages.
European Search Report for counterpart European Application No. 10013202, dated Jan. 28, 2011, 6 pages.
Office Action for counterpart Chinese Application No. 200680005586.4, dated Dec. 3, 2010, 13 pages.

\* cited by examiner

Monomer

Dimer

CANDLE AND CANDLE WAX CONTAINING METATHESIS AND METATHESIS-LIKE PRODUCTS

CROSS-REFERENCE TO RELATED APPLICATIONS

This application is a continuation of U.S. patent application Ser. No. 11/795,052, entitled CANDLE AND CANDLE WAX CONTAINING METATHESIS AND METATHESIS-LIKE PRODUCTS, filed May 15, 2008 which is a 371 of International Patent Application No. PCT/US06/00822, filed Jan. 10, 2006, and claims the benefit of priority thereto, and also claims priority U.S. Provisional Patent Application No. 60/642,600, filed Jan. 10, 2005; and to U.S. Provisional Patent Application No. 60/690,122, filed Jun. 13, 2005. The contents of both of these patent applications are incorporated herein in their entirety.

GOVERNMENT RIGHTS

This invention was made with U.S. Government support under Award Number DE-FG36-04G014016 awarded by the U.S. Department of Energy. The Government may have certain rights in the subject invention.

BACKGROUND

For a long time, beeswax was has been in common usage as a natural wax for candles. Some time ago, paraffin came into existence, in parallel with the development of the petroleum refining industry. Paraffin is produced from the residue leftover from refining gasoline and motor oils. Paraffin was introduced as a bountiful and low cost alternative to beeswax, which had become more and more costly and in more and more scarce supply.

Today, mineral wax-based paraffin is the primary industrial wax used to produce candles and other wax-based products. Conventional candles produced from this wax material typically emit a, smoke and can produce a bad smell when burning. In addition, a small amount of particles ("particulates") can be produced when the candle burns. These particles may affect the health of a human when breathed in. A candle that has a reduced amount of mineral wax-based paraffin would be preferable.

Accordingly, it would be advantageous to have other materials which can be used to form clean burning base wax for forming candles. If possible, such materials would preferably be biodegradable and be derived from renewable raw materials. The candle base waxes should preferably have physical characteristics, e.g., in terms of melting point, hardness and/or malleability, that permit the material to be readily formed into candles having a pleasing appearance and/or feel to the touch, as well as having desirable olfactory properties.

Additionally, there are several types of candles, including taper, votive, pillar, container candles and the like, each of which places its own unique requirements on the wax used in the candle. For example, container candles, where the wax and wick are held in a container, typically glass, metal or the like, require lower melting points, specific burning characteristics such as wider melt pools, and should desirably adhere to the container walls. The melted wax should preferably retain a consistent appearance upon resolidification.

In the past, attempts to formulate candle waxes from vegetable oil-based materials have often suffered from a variety of problems. For example, relative to paraffin-based candles, vegetable oil-based candles have been reported to exhibit one or more disadvantages such as cracking, air pocket formation, and a natural product odor associated with soybean materials. Various soybean-based waxes have also been reported to suffer performance problems relating to optimum flame size, effective wax and wick performance matching for an even burn, maximum burning time, product color integration and/or product shelf life. In order to achieve the aesthetic and functional product surface and quality sought by consumers of candles, it would be advantageous to develop new vegetable oil-based waxes that overcome as many of these deficiencies as possible.

Candles are often prepared by means of melt-processing. For purposes of commercial-scale manufacture, there can be economic advantage in the prospective utilization of wax powder compression technology. However, the production of a superior candle product by wax powder compression is not readily achieved. The compression-molding of a wax powder is affected by formulation variables, such as wax melting point, particle size distribution, cohesive nature of the wax, the number and quantity of additives such as air fresheners and colorants, and the like, and process variables, such as compression time and the degree of compression.

Today, candles are sold in the United States predominately for a decorating role and for adding ambiance to the home. An increasingly important aspect in marketing candles is the ability to deliver a fragrance. Here, candle manufacturers face constraints with the current wax systems due to chemical incompatibility of the fragrance and the petroleum-based waxes. In the preferred production methods (e.g., extrusion and compression molding), conventional materials have limited ability to hold fragrance. Overloading an extruded candle or compressed pillar candle with fragrance can lead to undesirable features, for example, fragrance weeping from the candle causing an oily surface and poor appearance.

There is continuing interest in the development of additional wax materials and candle products based on polyol ester materials, such as oilseed oils. In particular, there is a continuing interest in new wax materials which can be manufactured into candles by extrusion and compression technology.

SUMMARY

Figure 1:
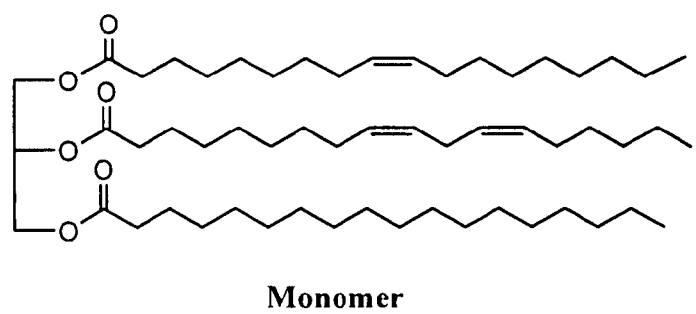
FIG. 1 is a chemical structure showing one embodiment of a polyol-ester monomer.

The present wax compositions comprise a product of a metathesis reaction and/or a compound or set of compounds that resemble the product of a metathesis reaction. The present wax compositions may be suitable for use in forming a candle and/or may provide a base wax composition that can be blended with other wax(es) and/or additional ingredients to form a candle wax. Such a candle would typically include a wick and the wax. The wax compositions may also include components not formed from a metathesis reaction (or resembling such products) including other waxes (e.g. a mineral wax, a natural wax, a paraffin wax and/or a hydrogenated vegetable oil).

The present wax compositions commonly include a polyol fatty acid ester component (made up of partial and/or completely esterified polyols), at least a portion of which have been subjected to a metathesis reaction and/or include compounds similar to those produced by a metathesis reaction. For example, the wax compositions may include a blend of (1) a hydrogenated metathesis product formed from a vegetable oil; and (2) a hydrogenated vegetable oil, e.g., a highly hydrogenated soybean oil. According to some embodiments, compounds formed by a metathesis reaction may include dibasic acid-containing polyol oligomers and/or compounds having an acid profile comprising one or more dibasic acids. The dibasic acid subunits are commonly derived from alpha, omega-dibasic acids, such octadecanedioic acid and corresponding alkanedioic acids having 21 or 24 carbon atoms. The dibasic-acid-polyol oligomers may contain any number of units, but in some embodiments contain at least one of a dimer, a trimer, and a tetramer, (i.e, the oligomer contains two, three, or four polyol subunits respectively) and may consist essentially of oligomers comprising eight or fewer polyol subunits. The dibasic acids may be unsaturated or may be saturated (e.g., where the oligomer is formed via a process which includes hydrogenation of the metathesis product of an unsaturated polyol fatty acid ester). The polymers may also comprise monobasic acid subunits which are esterified to other hydroxyl sites of the polyol subunit.

The present compositions relate to waxes which may be used in candles. Some embodiments of the waxes may have a low mineral-based paraffin content (e.g. no more than 50%, and potentially much lower amounts). The waxes may be formed from ester-based materials, such as vegetable oil-based wax which is generally a biodegradable material produced from renewable resources. Since some embodiments of the candles may be formed from a material with a low mineral-based paraffin content and may be substantially devoid of mineral-based paraffin (e.g. contain no more than about 0.5 wt. % paraffin), the candles according to these embodiments may emit little soot. The combination of low soot emission, biodegradability, and production from renewable raw material makes these embodiments particularly environmentally friendly products.

Certain embodiments of the present compositions include blends of a hydrogenated metathesized triacylglyceride stock and a highly hydrogenated triacylglyceride stock, commonly having an Iodine Value of no more than about 75 and, more suitably, an Iodine Value of about 50 or less. Suitable examples include blends of a metathesized vegetable oil that has been hydrogenated to an Iodine Value of no more than about 25 and a vegetable oil(s) which has been hydrogenated to an Iodine Value of about 25 or less. Such blends may be suitable for use as base wax compositions which, when combined with another wax material, e.g., a paraffin wax, may be particularly suitable for use in certain candle applications. For example, a blend of hydrogenated metathesized vegetable oil and hydrogenated vegetable oil, where the blend has an Iodine Value of no more than about 20 (and more suitably no more than about 10) can be combined with a higher melting paraffin wax (e.g., having a melting point of about 60° C. to 70° C.) to form a wax composition that is suitable for use in extrusion and/or compression molding of candles.

The present wax may be solid at room temperature, firm but not brittle, generally somewhat malleable, and/or have no free oil visible. The present wax may be particularly suited for use in forming many types of candles, such as container candles, votive candles, and pillar candles. The present waxes may also be capable of providing consistent characteristics, such as appearance, upon cooling and resolidification (e.g., after being burned in a candle) of the melted wax. In addition, it is often desirable that the wax is capable of being blended with natural color additives to provide an even, solid color distribution. It is also often desirable that the wax is capable of being blended with other additives, such as perfumes or other fragrances, and be capable of exhibiting good fragrance throw when the wax/fragrance blend is burned.

Metathesis product based waxes having a melting point of about 45° C. to 75° C. may be particularly advantageous for use in forming candles. Wax compositions of this type having a somewhat higher melting point, e.g., about 55° C. to 75° C. and, more commonly about 60° C. to 70° C. can be particularly desirable for use in forming votive and pillar candles. Metathesis product based waxes having a somewhat softer texture and/or lower melting point (e.g., about 45° C. to 60° C. and, more commonly about 50° C. to 55° C.) can be particularly suitable for forming container candles.

In many embodiments of the present application, a metathesis reaction may be carried out on a mixture which includes completely esterified polyol, such as triacylglycerides having unsaturated fatty acid groups, in the base stock. The metathesis reaction of a base stock including completely esterified polyols may also include one or more polyol partial esters, e.g., a fatty acid monoacylglyceride and/or fatty acid diacylglyceride. In these and other embodiments, the resulting composition may contain products formed by the metathesis reaction and/or products which resemble those formed by a metathesis reaction and optionally a subsequent hydrogenation.

In some embodiments, the wax composition may include other components such as a mineral wax, a free fatty acid, a natural wax (such as plant wax or insect wax), and/or other renewable resource based material. In many embodiments, the waxes not formed from renewable resources are preferably only present in the composition up to about 49% by weight, and often in much lower amounts. One such wax not formed from a renewable resource is a mineral wax. The mineral wax may be a petroleum wax such as a medium paraffin wax, a microcrystalline paraffin wax, and/or a petroleum wax obtained from crude oil refined to other degrees. Examples of natural waxes that may be employed include carnauba wax, candelila wax, montan wax, wool wax and/or beeswax. In some embodiments, the wax composition includes no more than about 25 wt. % of the waxes not formed from renewable resources. In still another embodiment, the wax composition includes no more than about 10% by weight of waxes not obtained from renewable resources.

In some embodiments, a candle with a string-less wick can be formed by suspending fine granular or powdered material, such as silica gel flour or wheat fiber in a vegetable oil such as soybean oil, cottonseed oil and/or palm oil. The inclusion of particulate material in a candle wax can result in a two-phase material and alter the visual appearance of a candle. In some embodiments, the wax is preferably substantially free (e.g., includes no more than about 0.5 wt. %) of particulate material. As used herein, the term "particulate material" refers to any material that will not dissolve in the wax when the wax is in a molten state.

The metathesis product based wax may also include minor amounts of other additives to modify the properties of the waxy material. Examples of types of additives which may commonly be incorporated into the present candles include colorants, fragrances (e.g., fragrance oils), antioxidants, light stabilizers, insect repellants, and migration inhibitors.

If the present wax is used to produce a candle, the same standard wicks that are employed with other waxes (e.g., paraffin and/or beeswax) can be utilized. In order to fully benefit from the environmentally-safe aspect of the present wax, it is desirable to use a wick which does not have a metal core, such as a lead or zinc core. One example of a suitable wick material is a braided cotton wick. Of course, any other type of wick may be used.

The present candles may be formed by a method which includes heating the metathesis product based wax to a molten state and introduction of the molten metathesis product based wax into a mold which includes a wick disposed therein. The molten metathesis product based wax is cooled in the mold to solidify the wax.

The present candles may also be formed by compression molding. This process is often carried out by introducing wax particles into a mold and applying pressure. The resulting candles may be over-dipped, in the same type or a different type of wax than used in the compression molding process. Of course, many other candle forming techniques may be used.

The metathesis product based wax may also be used to form other wax-based articles, for example, crayons, fire logs (wax with dispersed sawdust or agricultural waste), tarts, billets, sheets, profiles, and the like. Such articles may be prepared by mixing the wax with one or more ingredients and extruding or compressing the composition to form the wax-based article. For example, in one embodiment, the metathesis product based wax is extruded or molded to form a fire log comprising a fuel source, for example, sawdust. In another embodiment, the metathesis product based wax is extruded or molded to form a crayon comprising a pigment and optionally a filler. In another embodiment, the metathesis product based wax is extruded or molded to form a tart comprising a fragrance.

In another aspect the invention provides a composition of matter comprising a metathesis product formed from a base stock comprising a polyol fatty acid ester having a fatty acid composition that includes at least one unsaturated fatty acid; wherein the composition comprises less than about 1 wt. % hydrocarbons having a molecular weight of about 200 grams/mole or less. In some embodiments, the composition comprises less than about 1 wt. % hydrocarbons having a molecular weight of about 300 grams/mole or less. In some embodiments, the composition comprises less than about 0.1 wt. % hydrocarbons having a molecular weight of about 200 grams/mole or less. In other embodiments, the composition comprises less than about 0.1 wt. % hydrocarbons having a molecular weight of about 300 grams/mole or less.

The compositions may be prepared by a process comprising the steps of: (a) providing a polyol fatty acid ester having a fatty acid composition that includes at least one unsaturated fatty acid; (b) metathesizing the polyol fatty acid ester in the presence of a metathesis catalyst to produce a metathesis product comprising hydrocarbons, triacylglycerides, and triacylglyceride metathesis oligomers; and (c) distilling the metathesis product to remove at least a portion of the hydrocarbons. The distilling step may be conducted, for example, by steam stripping the composition.

In another aspect, the invention provides a composition of matter comprising a metathesis product formed from a base stock comprising a polyol fatty acid ester having a fatty acid composition that includes at least one unsaturated fatty acid; wherein the composition comprises about 30 wt. % or greater triacylglyceride metathesis pentamers and higher order oligomers. In some embodiments, the composition comprises about 40 wt. % or greater or about 50 wt % or greater triacylglyceride metathesis pentamers and higher order oligomers. The composition may be prepared from a base stock has a fatty acid profile comprising less than about 10 wt. % saturated fatty acids. Representative examples of base stocks include canola oil or linseed oil.

DETAILED DESCRIPTION

Many exemplary candles include portions formed from metathesis products and/or contain products which resemble those that would be formed from metathesis reactions. A potential precursor to the metathesis reaction is a polyol ester. A commonly available polyol ester is a vegetable oil. Vegetable oils tend to include significant amounts of fully esterified polyols formed from glycerol and fatty acids.

Metathesis is generally a catalytic reaction and involves the interchange of alkylidene units among olefinic hydrocarbons via the formation and cleavage of carbon-carbon double bonds. The metathesis reaction may occur between two of the same type of molecules, referred to as self-metathesis, and/or may occur between two dissimilar types of molecules, referred to as cross-metathesis.

The metathesis reaction may be reversible and may attain a thermodynamic equilibrium in which distribution of the alkylidene moieties is statistical. Further, the metathesis reaction product may be hydrogenated.

Definitions

As used herein, a "fully hydrogenated" vegetable oil refers to a vegetable oil which has been hydrogenated to an Iodine Value of no more than about 5. "Highly hydrogenated vegetable oil" refers to a vegetable oil which has been hydrogenated to an Iodine Value of no more than about 50. Although not always the case, such highly hydrogenated oils typically have a fatty acid composition which contains very little 18:2 fatty acid (typically no more than about 1 or 2 wt. % 18:2). The term "hydrogenated" fatty acid stock is used herein to refer to fatty acid ester-based stocks that are either partially or fully hydrogenated. Instead of employing a highly hydrogenated vegetable oil, a relatively saturated triacylglyceride material derived from precipitating a hard fat fraction from a vegetable oil may be employed. Hard fat fractions obtained in this manner are predominantly composed of triacylglycerides having saturated and mono-unsaturated monobasic acid acyl groups.

As used herein, "polyol esters" refers to esters produced from polyols. Polyols may include more than two hydroxyl groups. These polyols may comprise from two to about 10 carbon atoms, and may comprise from two to six hydroxyl groups, but other numbers of carbon atoms and/or hydroxyl groups are possible as well. The polyols may contain two to four hydroxyl moieties. Non-limiting examples of polyols include glycerin, 1,2-propanediol, 1,3-propanediol, 1,2-butanediol, 1,3-butanediol, 2,3-butanediol, 2-ethyl-1,3-propanediol, 2-ethyl-2-butyl-1,3-propanediol, neopentyl glycol, 2,2,4-trimethyl-1,3-pentanediol, trimethylolpropane (TMP), sorbitol and pentaerythritol. Neopentyl glycol, TMP, sorbitol, and pentaerythritol may also be common polyols. Very commonly, the polyol esters employed herein are esters of glycerin, e.g., triacylglycerides, or esters of a mixture of glycerin and one or more other polyols.

The polyol ester component may include a partial fatty acid ester of one or more polyols and/or a polyol which is fully esterified with fatty acids ("complete polyol fatty acid ester"). Examples of complete polyol fatty acid esters include triacylglycerides, propylene glycol diesters and tetra esters of pentaerythritol. Examples of suitable polyol partial esters include fatty acid monoglycerides, fatty acid diglycerides and sorbitan partial esters (e.g., diesters and triesters of sorbitan). In some embodiments, the polyol may include from 2 to 6 carbon atoms and 2 to 6 hydroxyl groups. Examples of suitable polyols include glycerol, trimethylolpropane, ethylene glycol, propylene glycol, pentaerythritol, sorbitan and sorbitol.

Polyol esters can be produced by transesterification of a polyol with methyl esters of an acid. The acids may be fatty acids. The fatty acid may be a straight chained or branched chain fatty acid. For example, 2-ethyl hexanoic acid is a potential branched chain fatty acid. The fatty acids may be saturated or be unsaturated. Further, the fatty acids may be monobasic, dibasic, or contain some other number of acyl functional groups.

The acyl portion in the present polyol esters can be derived from any number of sources. For instance, it can be a fatty acid derived from monoglycerides, diglycerides, triglycerides, esters, free fatty acids, and/or other sources of acyl groups. The non-acyl portion ("R group") of the acyl group can be straight or branched, saturated or unsaturated, and/or contain non-carbon substituents including oxygen (such as hydroxyl groups), sulfur and/or nitrogen. The acyl groups may include an R group which is an alkyl group, an alkenyl group, or a hydroxy substituted alkyl group. Many of the R groups may be straight chain saturated hydrocarbon groups ("straight chain alkyl groups") and/or straight chain monounsaturated hydrocarbon groups ("straight chain alkenyl groups").

The mixture of acids isolated from complete hydrolysis of the polyol ester in a specific sample is referred to herein as the "acid composition" of that sample. By the term "acid composition" reference is made to the identifiable acid residues in the various esters. The distribution of acids in a particular mixture of esters may be readily determined by methods known to those skilled in the art.

In general, oils extracted from any given plant or animal source comprise a mixture of triacylglycerides characteristic of the specific source. The mixture of fatty acids isolated from complete hydrolysis of the triacylglycerides and/or other fatty acid esters in a specific sample are referred herein to as the "fatty acid composition" of that sample. By the term "fatty acid composition" reference is made to the identifiable fatty acid residues in the various esters. The distribution of fatty acids in a particular oil or mixture of esters may be readily determined by methods known to those skilled in the art, e.g., via gas chromatography or conversion to a mixture of fatty acid methyl esters followed by analysis by gas chromatography.

The method(s) described herein can be used to provide candles from triglyceride-based materials having a melting point and/or solid fat content which imparts desirable molding and/or burning characteristics. The solid fat content as determined at one or more temperatures is a measure of the fluidity properties of a triglyceride stock. Solid fat content ("SFC") can be determined by Differential Scanning calorimetry ("DSC") using the methods well known to those skilled in the art. Fats with lower solid fat contents have a lower viscosity, i.e., are more fluid, than their counterparts with high solid fat contents.

Metathesis Products and Metathesis-Like Products

Products of a metathesis reaction, particularly a self-metathesis reaction, may include one or more identifiable properties and/or compounds. Products formed from polyol esters may include characteristic acids in an acid profile and may contain oligomers of the polyol ester. As one example of a characteristic compound, when a substantial amount of reactant comprises monobasic acids having carbon-carbon double bonds (such as oleic acid) a metathesis product may include dibasic acid in the acid profile of the composition. The reactant of this example may include free monobasic acids and may include esters of monobasic acids. In some embodiments, the acid profile may comprise at least about 1 wt. % dibasic acids. Further, in some of these embodiments the acid profile may comprise at least about 4 wt. % dibasic acids. Further still, in some of these embodiments the acid profile may comprise at least about 15 or 20 wt. % dibasic acids. The dibasic acid may include terminal carboxylic acid groups (e.g. $HO_2C-(CH_2)_{16}-CO_2H$). In some embodiments, linear terminal C18, C21, and/or C24 diacids may be the predominant types of dibasic acids present. In some of these embodiments, the acid profile may comprise a lower amount of dibasic acids (e.g., no more than 10% of the total dibasic acids) that have fewer than about 18 carbon atoms and/or more than about 30 carbon atoms.

According to some embodiments, an alkene molecule may be used to extend or otherwise vary the length of a starting acid molecule (such as a fatty acid molecule) using a metathesis reaction. This may result in an increase in the chain length or an increased variance in the chain length of the acids in the acid profile compared to the starting material. In some embodiments where a vegetable oil is used as a reactant in the metathesis reaction, a glycerol ester may have a fatty acid profile including a higher percentage of high chain length fatty acids than normally found in a vegetable oil and/or than in the reactants generally. In some embodiments where a vegetable oil is used as a reactant in the metathesis reaction, a glycerol ester may have a fatty acid profile that includes a greater variety of chain length fatty acids than normally found in a vegetable oil and/or than in the reactants generally.

The long chain acids, the changed variety of acids, and/or the dibasic acids may be unsaturated or may be saturated. These acids may be straight chained or may be branched. These acids may be hydroxylated or may be non-hydroxylated. These acids may comprise at least about 12 or 18 carbons atoms and may comprise up to about 24 or 30 carbon atoms. These acids may be acyl groups of fully or partially esterified polyols such as a glycerol ester.

Figure 2:
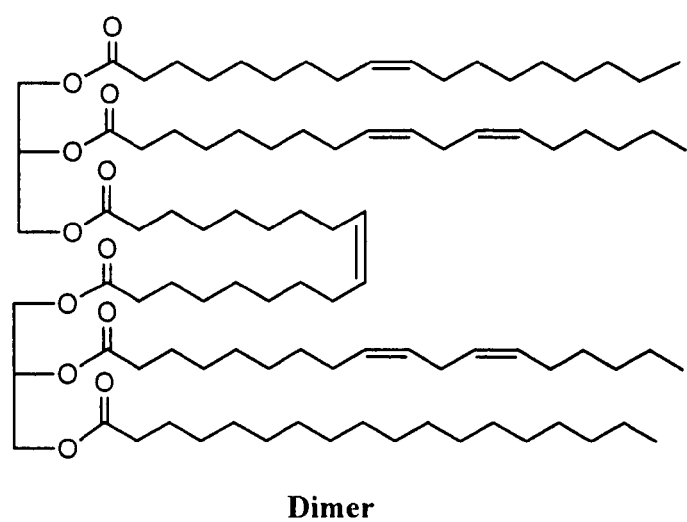
FIG. 2 is a chemical structure showing one embodiment of a polyol-ester dimer.
Figure 3:
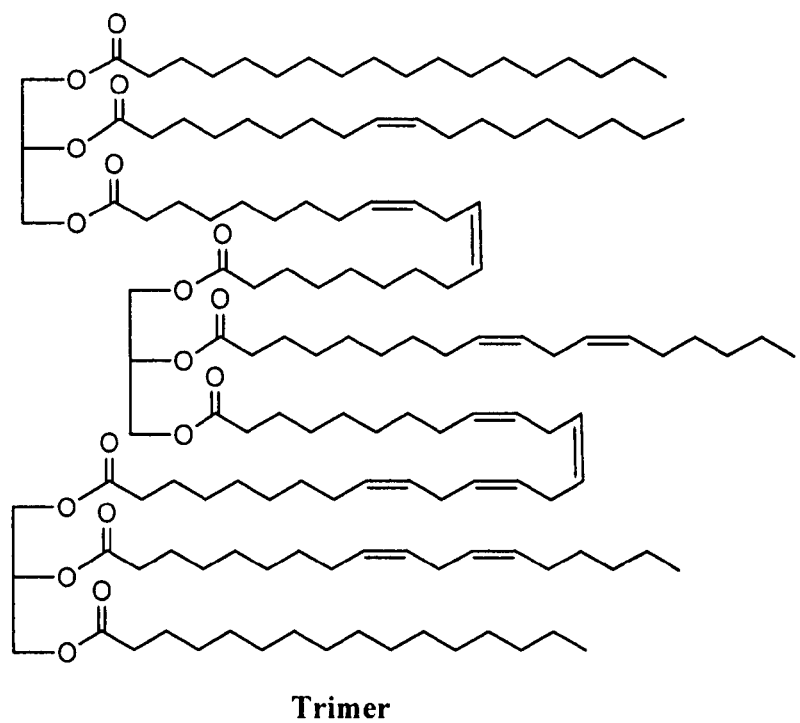
FIG. 3 is a chemical structure showing one embodiment of a polyol-ester trimer.

If an ester (which is used to refer to the ester and/or to precursors which may be used to form the ester) having an acid portion comprising a carbon-carbon double bond is subjected to a metathesis reaction with a substantial amount of similar esters, the product may include dibasic acid alcohol polymers (e.g. dimers, trimers, tetramers, etc. of alcohols linked by dibasic acids) in the composition. These polymers would comprise multiple alcohol units (such as polyols) connected together by dibasic acids. In some embodiments, the ester may be formed from a polyol. Polyols may be more conducive to forming the higher unit number polymers (trimers, tetramers, etc.). FIG. 1 is a chemical structure depicting one embodiment of a polyol-ester monomer. FIG. 2 is a chemical structure depicting one embodiment of a polyol-ester dimer. FIG. 3 is a chemical structure depicting one embodiment of a polyol-ester trimer.

In some embodiments, the product includes at least one of a dimer, a trimer, and a tetramer of a dibasic acid alcohol polymer (particularly a dibasic acid-containing polyol polymer, such as oligomers produced by metathesis of unsaturated fatty acid triglycerides, e.g., soybean oil). According to many of these embodiments, the polyol component comprises glycerol and the dibasic acid component comprises straight chain dibasic acids (e.g. linear alkane and/or linear alkene diacids). In some embodiments, the product contains more tetramers and/or higher unit number oligomers than dimers or trimers, and in some of these embodiments contain more tetramers and/or higher unit oligomers than dimers and trimers combined. As described in the Experimental section herein, the relative amount of dimers, trimers, tetramers and higher unit oligomers may be characterized, for example, in terms of "area %" as determined by the HPSEC/ELSD procedure described therein. In some embodiments, the product comprises at least about 30 area % tetramers and/or other higher unit oligomers or at least about 40 area % tetramers and/or other higher unit oligomers. In some embodiments, the product comprises no more than about 60 area % tetramers and/or other higher unit oligomers or no more than about 50 area % tetramers and/or other higher unit oligomers. In other embodiments, the product comprises no more than about 1 area % tetramers and/or other higher unit oligomers. In some embodiments, the product comprises at least about 5 area % dimers or at least about 15 area % dimers. In some embodiments, the product comprises no more than about 25 area % dimers. In some of these embodiments, the product comprises no more than about 20 area % dimers or no more than about 10 area % dimers. In some embodiments, the product comprises at least 1 area % trimers. In some of these embodiments, the product comprises at least about 10 area % trimers. In some embodiments, the product comprises no more than about 20 area % trimers or no more than about 10 area % trimers. According to some of these embodiments, the product comprises no more than 1 area % trimers.

In some embodiments, a metathesis product may comprise dibasic-acid-polyol polymers. In some of these embodiments, the dibasic-acid-polyol polymers may comprise cyclic polymers. In some embodiments, the dibasic-acid-polyol polymers may comprise more polymers having 4 or more units than polymers having 3 or fewer units.

In some embodiments, a metathesis product may comprise molecules where a single dibasic acid is bonded to more than one hydroxyl site of a single polyol.

According to many embodiments that include a polyol, the polyol may include glycerol and/or the acid profile may comprise fatty acids. According to some embodiments, the polyol consists essentially of glycerol. According to some embodiments, the acid profile consists essentially of fatty acids and/or dibasic acids. Each reference to and/or limitation on a polyol ester polymer (as discussed above) could be applied, in many of these embodiments, to a fully esterified polyol ester of glycerol and fatty acids (e.g. triacylglycerides derived from a vegetable oil). If the reaction consists essentially of triacylglycerides of fatty acids, then the resulting metathesis product will likely comprise an acid profile that includes dibasic acids of fatty acids (i.e. the types dibasic acids that would tend to be formed from the use of the types of unsaturated acids typically found in fatty acid profiles). The acid profile would also likely include monobasic acids of chain lengths ranging from 12 carbons to at least 30 carbons.

Vegetable oils and other lipid based materials tend to comprise a distribution of different types of esters—the different types formed by different combinations of fatty acid portions. The typical distribution that may be found may be different for different types of lipid-based materials. In many cases, the distribution may not be representative of a statistical distribution. Of course, the metathesis product made from these esters may or may not comprise a statistical distribution of the various types of esters.

In some embodiments, the metathesis product may reach a point where it contains fewer unsaturated acids than the starting material. In embodiments where the starting material is a fatty acid polyol based material (e.g. triacylgylcerol from a soy oil), there may be fewer unsaturated fatty acids in the fatty acid profile than in the starting material. In some embodiments having esters of fatty acids, the metathesis product may comprise no more than about 2 area % 18:3 fatty acids in the fatty acid profile. In some of these embodiments, the metathesis product may comprise no more than about 1 area % 18:3 fatty acids in the fatty acid profile. In some embodiments, the metathesis product may comprise no more than about 30 wt. % 18:2 fatty acids in the fatty acid profile. In some of these embodiments, the metathesis product may comprise no more than about 20 wt. % or no more than about 10 wt. % 18:2 fatty acids in the fatty acid profile. In some embodiments, the metathesis product may comprise no more than about 20 wt. % 18:1 fatty acids in the fatty acid profile. In some of these embodiments, the metathesis product may comprise no more than about 10 wt. % 18:1 fatty acids in the fatty acid profile.

In some embodiments, the metathesis product may be a hydrogenated version of the products of a metathesis reaction. In these embodiments the product may include fewer dibasic acids in an acid profile that are unsaturated than are saturated. In some embodiments where the starting material is a fatty acid polyol based product, the product may comprise no more than about 1 wt. % 18:3 fatty acids in its fatty acid profile. In some embodiments, the product may contain no more than about 5 wt. % or no more than about 1 wt. % 18:2 fatty acids in its fatty acid profile. In some embodiments, the product may contain no more than about 5 wt. % or no more than about 1 wt. % 18:1 fatty acids in its fatty acid profile. In some embodiments, the fatty acid profile of the product comprises at least about 0.2 wt. % or at least about 1 wt. % 12:0 fatty acids. In some embodiments, the product has a fatty acid profile comprising no more than about 10 wt. % or no more than about 3 wt. % trans fatty acids.

In some embodiments, the metathesis reaction product of a fatty acid based polyol ester may comprise fatty acid components that are not typically found in oil-based fatty acid profiles. For example, a metathesis product may comprise 15:1 or 15:0 fatty acids. According to some embodiments, the fatty acid profile comprises fatty acids having 15 carbon atoms. This may include at least about 2 wt. % fatty acids having 15 carbons. According to some of these embodiments, the fatty acid profile may include at least about 4 wt. % or at least about 10 wt. % fatty acids having 15 carbons. As another example, the fatty acid profile may comprise 21:1 or 21:0 fatty acids. According to some embodiments, the fatty acid profile comprises fatty acids having 21 carbon atoms.

In some embodiments (e.g., when the metathesis product is hydrogenated), there may be a large concentration of hydrocarbons. In some embodiments, the metathesis product comprises about 1 to about 50 wt. % hydrocarbons. In others of these embodiments, the hydrocarbons are removed from the metathesis product. In these embodiments, the metathesis product comprises no more than about 1 wt. % hydrocarbons, and potentially no more than about 0.5 wt. % hydrocarbons. In some embodiments the hydrocarbons are straight chain hydrocarbons. In some embodiments, the hydrocarbons comprise from about 6 to about 30 carbons atoms, and in some of these may comprise at least about 15 and/or no more than about 24 carbon atoms. In some embodiments, the hydrocarbons have a median or center weight of about 18 to about 21 carbons. In some embodiments, the hydrocarbons have a median or center weight of about 20 carbons. In some embodiments, the hydrocarbons at least include hydrocarbons having about 6 to about 9 hydrocarbons.

It should be understood that a metathesis product may, and typically does, include combinations of the above mentioned properties. Also, it should be understood that a metathesis-like product can include one or more of the above mentioned properties or molecular compositions whether or not it was created using a metathesis reaction.

Method for Producing Metathesis Products

Any known or future-developed metathesis catalyst may be used, alone or in combination with one or more additional catalysts, in accordance with embodiments of the present method. Exemplary metathesis catalysts used can include metal carbene catalysts based upon transition metals, such as ruthenium. Exemplary ruthenium-based metathesis catalysts include those commercially available catalysts represented by structures 12 (commonly referred to as Grubbs's catalyst), 14 and 16, where Ph is phenyl, Mes is mesityl, and Cy is cyclohexyl.

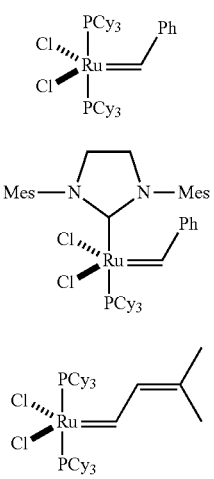

12

14

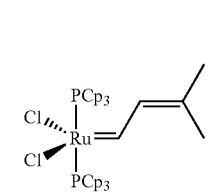

16

Structures 18-28, illustrated below, represent additional potential ruthenium-based metathesis catalysts. Techniques for using catalysts 12-28, as well as additional related metathesis catalysts are known in the art.

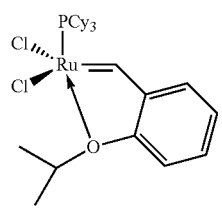

18

20

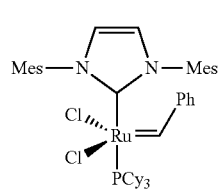

22

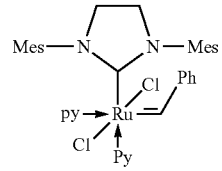

24

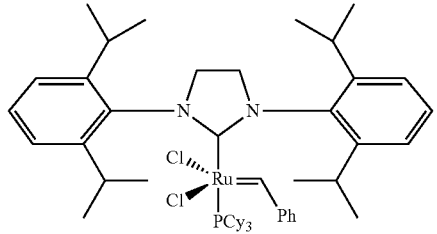

26

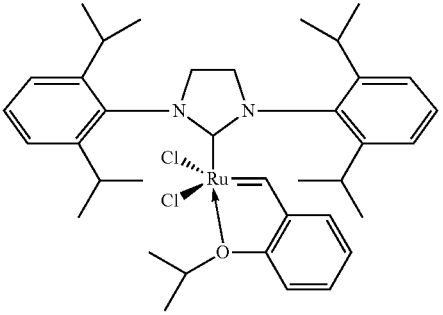

28

Catalysts C627, C712, C823 and C827, where Cy is cyclohexyl, are additional ruthenium based catalysts (which are commercially available from Materia) which may be employed in the metathesis reactions in the present methods.

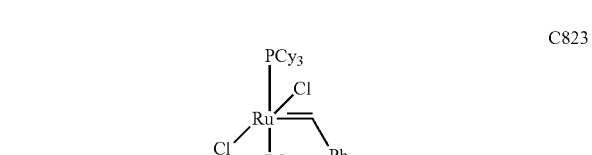

C823

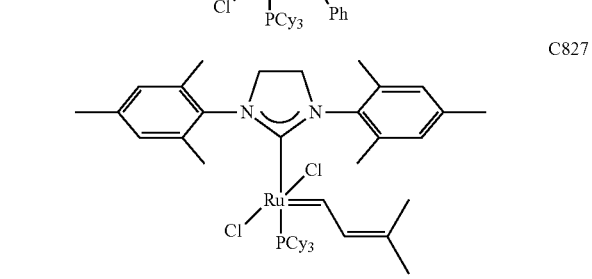

C827

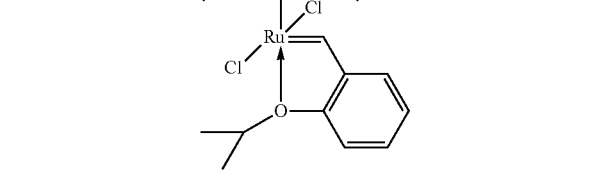

C627

-continued

C712

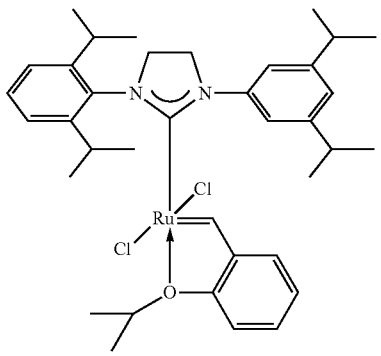

Additional exemplary metathesis catalysts include, without limitation, metal carbene complexes selected from the group consisting of molybdenum, osmium, chromium, rhenium, tungsten and tungsten carbene complexes. The term "complex" refers to a metal atom, such as a transition metal atom, with at least one ligand or complexing agent coordinated or bound thereto. Such a ligand typically is a Lewis base in metal carbene complexes useful for alkene, alkyne or alkene-metathesis. Typical examples of such ligands include phosphines, halides and stabilized carbenes. Some metathesis catalysts may employ plural metals or metal co-catalysts (e.g. a catalyst comprising a tungsten halide, a tetraalkyl tin compound, and an organoaluminum compound).

An immobilized catalyst can be used for the metathesis process. Such an immobilized catalyst may be used in a flow process. An immobilized catalyst can simplify purification of products and recovery of the catalyst so that recycling the catalyst may be more convenient.

The metathesis process for producing industrial chemicals can be conducted under any conditions adequate to produce the desired metathesis product or products. For example, stoichiometry, atmosphere, solvent, temperature and pressure can be selected to produce a desired product and to minimize undesirable by-products. The metathesis process may be conducted under an inert atmosphere. Similarly, if an olefin or alkyne reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen and combinations thereof.

Similarly, if a solvent is used, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc.

In certain embodiments, a ligand may be added to the metathesis reaction mixture. In many embodiments using a ligand, the ligand is selected to be a molecule that stabilizes the catalyst, and may thus provide an increased turnover number for the catalyst. In some cases the ligand can alter reaction selectivity and product distribution. Examples of ligands that can be used include Lewis base ligands, such as, without limitation, trialkylphosphines, for example tricyclohexylphosphine and tributyl phosphine; triarylphosphines, such as triphenylphosphine; diarylalkylphosphines, such as, diphenylcyclohexylphosphine; pyridines, such as 2,6-dimethylpyridine, 2,4,6-trimethylpyridine; as well as other Lewis basic ligands, such as phosphine oxides and phosphinites. Additives may also be present during metathesis that increase catalyst lifetime.

Using currently known catalysts, the metathesis processing temperature may largely be a rate-dependent variable where the temperature is selected to provide a desired product at an acceptable production rate. The selected temperature may be greater than about −40° C., may be more than about −20° C., and is generally selected to be more than about 0° C. or more than about 20° C. Generally, the process temperature may be no more than about 150° C., and may be no more than about 120° C. Thus, an exemplary temperature range for the metathesis reaction may be from about 20° C. to about 120° C. Lower temperatures can be used, for example, to minimize the production of undesired impurities or to favor a particular reaction pathway.

The metathesis process can be conducted under any pressure of gaseous alkene, alkyne and/or diluent. The total pressure may be selected to be greater than about 30 kPa, and may be greater than about 100 kPa. Generally, the total pressure may be no more than about 7,000 kPa, and may be no more than about 3,000 kPa. Therefore, an exemplary pressure range for the metathesis process conducted under pressure is from about 100 kPa to about 3,000 kPa.

Any useful amount of the selected metathesis catalyst can be used in the current process. If the catalyst has a relatively high turnover number, the molar ratio of the metathesis process precursor, such as an unsaturated fatty acid or fatty acid derivative, to the catalyst may be a ratio up to about 10,000,000 to 1, but may be no more than about 500,000 to 1. The molar ratio of the unsaturated reactants to the catalyst may be more than about 5 to 1, and may be more than about 50 to 1 or about 100 to 1.

Mineral Wax Mixtures

A composition may also be formed by combining a metathesis or metathesis-like product with a mineral wax. Some examples of mineral waxes include mineral waxes such as montan wax, peat wax, and petroleum waxes (petrolatum, paraffin wax, ozokerite and ceresin waxes).

Petroleum wax tends to be one of the more widely used waxes for current candles. The petroleum wax can be a by-product of the petroleum refining process and may be obtained commercially from suppliers such as Sonneborn (Tarrytown, N.Y.). The quality and quantity of the wax obtained from the refining process is dependent upon the source of the crude oil and the extent of the refining. The petroleum wax component of the wax composition includes, for example, a paraffin wax, including medium paraffin wax, microcrystalline paraffin wax or a combination thereof. However, petroleum wax obtained from crude oil refined to other degrees may also be used.

Although the exact chemical compositions of these waxes are not known as the nature of these by-products vary from one distillation process to the next, these waxes tend to be composed of various types of hydrocarbons. For example, medium paraffin wax is generally composed primarily of straight chain hydrocarbons having carbon chain lengths ranging from about 20 to about 40, with the remainder typically comprising isoalkanes and cycloalkanes. The melting point of medium paraffin wax is typically about 50° C. to about 65° C. Microcrystalline paraffin wax is generally composed of branched and cyclic hydrocarbons having carbon chain lengths of about 30 to about 100 and the melting point of the wax is typically about 60° C. to about 90° C. Further descriptions of the petroleum wax that may be used may be found in Kirk-Othmer, Encyclopedia of Chemical Technology, 3rd Edition, Volume 24, pages 473-76, which is hereby incorporated by reference.

The wax portions of suitable compositions typically have mineral wax portions which are no more than 50 wt. % of the wax portion of the composition, with polyol ester compositions making up at least half of the wax portion. The polyol ester portions can include transesterified polyol ester portions and/or non-transesterified polyol ester portions. The polyol ester portions are preferably based on triglycerol and also preferably have fatty acid portions. Other suitable compositions have up to about 25 wt. % and up to about 17 wt. % mineral wax. Other suitable compositions have no more than about 5 wt. % but more than 0 wt. % mineral wax. These compositions preferably have no more than about 3 wt. % mineral wax, and more preferably, no more than about 1 wt. % mineral wax. If a mineral wax is used, it is typically a petroleum wax, such as paraffin wax.

Other Materials

Natural waxes and synthetic waxes may be used in combination with a metathesis or metathesis-like product to form a composition. For instance, many creatures (such as insects and animals) and plants form waxy substances that are generally solid at room temperature. Some example of the various types of solid natural creature waxes are beeswax, lanolin, shellac wax, chinese insect wax, and spermaceti. Some of the examples of the various types of natural plant waxes are carnauba, candelila, japan wax, ouricury wax, rice-bran wax, jojoba wax, castor wax, bayberry wax, sugar cane wax, and maize wax. Natural waxes may also be formed from hydrogenating or otherwise modifying a lipid-based material such as a vegetable oil so that it is substantially solid at room temperature.

Additionally, synthetic waxes may be used. For instance, waxes such as polyethylene wax, Fischer-Tropsch wax, chlorinated naphthalene wax, chemically modified wax, substituted amide wax, alpha olefins and polymerized alpha olefin wax may be used. Waxes may also be formed from polyolester-based materials, including esters other than triacylglyceride. The present wax compositions may also include other synthetic materials, such as an ethylene vinyl acetate copolymer, an ethylene alpha-olefin copolymer, a silicone, a PTFE material, free fatty acid, and/or fatty acid amide.

One or more of the above mentioned waxes and natural-based materials may be used in combination with the metathesis product or metathesis-like product to form a suitable material for use in a candle wax.

Renewable Resource Materials

According to some preferred embodiments, the metathesis-based wax would comprise materials derived from a renewable resource. These materials may include the natural waxes discussed above and may include materials such as lipid-based materials that are not waxy. Examples of lipid-based materials may include oils derived from plants such as soy oil, palm oil, sunflower oil, and other oils discussed in this application. These oils may be refined, may be bleached, may be fractionated, may be fully or partially hydrogenated, or may be otherwise modified from their original state. A highly hydrogenated oil that may be used may have an Iodine Value of no more than about 10. A less hydrogenated (or unhydrogenated) oil that may be used may have an Iodine Value of at least about 50 or at least about 75. The renewable resource based materials may also include other materials that are based on fatty acid portions such as monoacyl glyceride (e.g. glycerol monostearate) and diacylglyceride (e.g. glycerol distearate).

According to some embodiments, a wax includes at least 50 wt. % materials derived from renewable resources. According to some of these embodiments, the wax may include at least about 70 or at least about 85 wt. % materials derived from renewable resources. The material used to meet these limitations may be entirely or substantially derived from plant and/or insect sources and may include at least a substantial portion derived from plant oils. This material may include the metathesis product where the reactants of the metathesis product are derived from a renewable resource such as a plant oil.

In some embodiments, it may be advantageous to have a wax that is slightly tackier relative to the other candle waxes described herein. Such slightly tackier waxes may be employed in some extrusion molding processes. According to some of these embodiments, such a wax for use in extrusion processes may be formed using a fatty-acid-based component that has larger amounts of di-unsaturated or tri-unsaturated fatty acids in its fatty acid profile. For example, in addition to a fully hydrogenated soybean metathesis product, the wax may include a fatty-acid-based component having an Iodine Value of at least about 80 (e.g., a partially hydrogenated oilseed oil having an Iodine value of about 80 to 100). According to some of these embodiments, the wax may comprise at least about 5 wt. % (e.g., about 5 to 20 wt. %) or at least about 10 wt. % of the partially hydrogenated oilseed oil meeting this Iodine Value criteria. The slightly tackier waxes may also include a paraffin component and may desirably have fatty-acid-based component that includes about 1 to 10 wt. % polyunsaturated fatty acids in its fatty acid profile (e.g., a triglyceride material with a fatty acid profile which has about 2 to 10 wt. % 18:2 fatty acid and no more than about 0.2 wt. % tri-unsaturated fatty acids).

In other embodiments, it may be more advantageous to have a wax that can be molded by compression (e.g. some compression molding processes). According to some of these embodiments, such a wax may be formed using a fatty-acid-based component that has smaller amounts of di-unsaturated or tri-unsaturated fatty acids in its fatty acid profile. According to some embodiments, the wax includes a fatty acid-based component having that is substantially lacking (e.g., no more than about 2 wt. % and preferably less than 1 wt. % di-unsaturated and/or tri-unsaturated fatty acids) polyunsaturated fatty acids) in its fatty acid profile.

Kits

The candle wax may be packaged as part of a candle-making kit, e.g., in the form of beads or flakes of wax, which includes also typically would include instructions with the candle wax. The candle-making kit typically would also include material which can be used to form a wick.

Performance Enhancing Additives

A wide variety of coloring and scenting agents, well known in the art of candle making, are available for use with waxy materials. Typically, one or more dyes or pigments are employed to provide the desired hue to the color agent, and one or more perfumes, fragrances, essences or other aromatic oils are used to provide the desired odor to the scenting agent. The coloring and scenting agents generally also include liquid carriers which vary depending upon the type of color- or scent-imparting ingredient employed. The use of liquid organic carriers with coloring and scenting agents is preferred because such carriers are compatible with petroleum-based waxes and related organic materials. As a result, such coloring and scenting agents tend to be readily absorbed into waxy materials. It is especially advantageous if a coloring and/or scenting agent is introduced into the waxy material when it is in the form of prilled granules.

The colorant is an optional ingredient and is commonly made up of one or more pigments and dyes. Colorants are typically added in a quantity of about 0.001-2 wt. % of the waxy base composition. If a pigment is employed, it is typically an organic toner in the form of a fine powder suspended in a liquid medium, such as a mineral oil. It may be advantageous to use a pigment that is in the form of fine particles suspended in a vegetable oil, e.g., an natural oil derived from an oilseed source such as soybean or corn oil. The pigment is typically a finely ground, organic toner so that the wick of a candle formed eventually from pigment-covered wax particles does not clog as the wax is burned. Pigments, even in finely ground toner forms, are generally in colloidal suspension in a carrier.

If a dye constituent is utilized, it may be dissolved in an organic solvent. A variety of pigments and dyes suitable for candle making are listed in U.S. Pat. No. 4,614,625, the disclosure of which is herein incorporated by reference. The preferred carriers for use with organic dyes are organic solvents, such as relatively low molecular weight, aromatic hydrocarbon solvents; e.g. toluene and xylene. The dyes ordinarily form true solutions with their carriers. Since dyes tend to ionize in solution, they are more readily absorbed into the prilled wax granules, whereas pigment-based coloring agents tend to remain closer to the surface of the wax.

Candles often are designed to appeal to the olfactory as well as the visual sense. This type of candle usually incorporates a fragrance oil in the waxy body material. As the waxy material is melted in a lighted candle, there is a release of the fragrance oil from the liquefied wax pool. The scenting agent may be an air freshener, an insect repellent or more serve more than one of such functions.

The air freshener ingredient commonly is a liquid fragrance comprising one or more volatile organic compounds which are available from perfumery suppliers such IFF, Firmenich Inc., Takasago Inc., Belmay, Noville Inc., Quest Co., and Givaudan-Roure Corp. Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose and the like.

A wide variety of chemicals are known for perfumery such as aldehydes, ketones, esters, alcohols, terpenes, and the like. A fragrance can be relatively simple in composition, or can be a complex mixture of natural and synthetic chemical components. A typical scented oil can comprise woody/earthy bases containing exotic constituents such as sandalwood oil, civet, patchouli oil, and the like. A scented oil can have a light floral fragrance, such as rose extract or violet extract. Scented oil also can be formulated to provide desirable fruity odors, such as lime, lemon or orange.

Synthetic types of fragrance compositions either alone or in combination with natural oils such as described in U.S. Pat. Nos. 4,314,915; 4,411,829; and 4,434,306; incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like. The scenting agent can also be a liquid formulation containing an insect repellent such as citronellal, or a therapeutic agent such as eucalyptus or menthol. Once the coloring and scenting agents have been formulated, the desired quantities are combined with waxy material which will be used to form the body of the candle. For example, the coloring and/or scenting agents can be added to the waxy materials in the form of prilled wax granules. When both coloring and scenting agents are employed, it is generally preferable to combine the agents together and then add the resulting mixture to the wax. It is also possible, however, to add the agents separately to the waxy material. Having added the agent or agents to the wax, the granules are coated by agitating the wax particles and the coloring and/or scenting agents together. The agitating step commonly consists of tumbling and/or rubbing the particles and agent(s) together. Preferably, the agent or agents are distributed substantially uniformly among the particles of wax, although it is entirely possible, if desired, to have a more random pattern of distribution. The coating step may be accomplished by hand, or with the aid of mechanical tumblers and agitators when relatively large quantities of prilled wax are being colored and/or scented.

Certain additives may be included in the present wax compositions to decrease the tendency of colorants, fragrance components and/or other components of the wax to migrate to an outer surface of a candle. Such additives are referred to herein as "migration inhibitors." The wax may include 0.1 to 5.0 wt. % of a migration inhibitor. One type of compounds which can act as migration inhibitors are polymerized alpha olefins, more particularly polymerization products formed from alpha olefins having at least 10 carbon atoms and, more commonly from one or more alpha olefins having 10 to about 25 carbon atoms. One suitable example of such as polymer is an alpha olefin polymer sold under the tradename Vybar® 103 polymer (mp 168° F. (circa 76° C.); available from Baker-Petrolite, Sugarland, Tex.). The inclusion of sorbitan triesters, such as sorbitan tristearate and/or sorbitan tripalmitate and related sorbitan triesters formed from mixtures of fully hydrogenated fatty acids, in the present wax compositions may also decrease the propensity of colorants, fragrance components and/or other components of the wax to migrate to the candle surface. The inclusion of either of these types of migration inhibitors can also enhance the flexibility of the base wax material and decrease its chances of cracking during the cooling processes that occurs in candle formation and after extinguishing the flame of a burning candle. For example, it may be advantageous to add up to about 5.0 wt. % and, more commonly, about 0.1-2.0 wt. % of a migration inhibitor, such as an alpha olefin polymer, to the present wax materials.

Manufacturing of high fragrance paraffin candles by extrusion and compression wax may be impeded by the incompatibility of the fragrance and the paraffin wax. In extrusion, at high fragrance loading, the wax is not able to solubilize the fragrance leaving a two-phase system in the barrel of the extruder. This causes fragrance to leak out of the extruder dye leaving an inferior candle product and lower fragrance incorporation. Typically, extruded candle formulations are limited to about 3 wt. % fragrance. In compression molding, high fragrance loading with paraffin wax causes the wax to become too tacky to process. After the compression cycle, the wax tends to stick to the compression mold causing defects in the candle as well as potential disruption to the production process. Typically, compression candles formulations are limited to about 1.5% fragrance.

In some embodiments, the wax compositions of the invention have improved fragrance holding ability as compared to wax composition that do not include metathesis products. Increased fragrance holding is desirable, for example, in order to provide a candle with a stronger scent when burned. When included in the present wax compositions, fragrance is typically included in, an amount up to about 15 wt. %. When the wax composition is intended for use in a compression molded candle, the wax composition typically comprises about 1.5 wt. % or greater fragrance, for example, about 1.5 to 6 wt. % fragrance or about 3 to 6 wt. % fragrance. When the wax composition is intended for use in an extruded candle, the wax composition typically comprises about 3 wt. % or greater fragrance, for example, about 3 to 6 wt. % fragrance.

The present candle wax may also include an antioxidant, e.g., about 1 ppm to about 10 ppm of an antioxidant such as t-butylhydroquinone (TBHQ) or butylated hydroxytoluene (BHT), to enhance the oxidative stability of the wax and increase shelf life. Other suitable antioxidants that may be employed are well known in the art, and include, without limitation, dihydroxytoluene, stearic hydrazide, 2,6-di-tert-butyl-4-methylphenol, Irganox® 1010 hindered phenol antioxidant (available from Ciba Specialty Chemicals (Tarrytown, N.Y.)). Sodium ethylenediaminetetraacetic acid and/or other metal chelating agent may be employed to enhance the effectiveness of such antioxidant. Light stabilizers such as UV absorbers (e.g., benzophenones and benzotriazoles), free radical scavengers, and hindered amine light stabilizers (HALS) may also be employed. Examples are commercially available from Ciba Specialty Chemicals (Tarrytown, N.Y.).

Exemplary Properties of Candle Waxes

The exemplary waxes include a metathesis product or metathesis-like product. The metathesis product may include a polyol ester component. The polyol ester component can be a complete ester (fully esterified), or can be an incomplete ester (having potential ester bonding sites of the polyol not occupied by acyl groups).

The metathesis product components of the waxes are preferably formed by a metathesis reaction of a precursor mixture. The precursor mixture may include polyol esters, free fatty acids, polyols, other esters, and/or other components. Some polyol esters which are particularly well suited include polyol esters of fatty acids. Some typical polyol esters include monoacylglyceride, diacylglyceride, and triacylglyceride. Linked glyceride esters may also be used. Further, glycerin and other glycerol related molecules (e.g. polyglycerol) may be used as part of the polyol mixture. The precursor mixture would preferably include a polyol based ester mixture having an acid composition with a significant percentage of unsaturated fatty acids.

The precursor mixture could use natural, refined, and/or hydrogenated oils/fats, such as plant oils, as part of the precursor mixture. Typical plant oils/fats include palm oil, palm kernel oil, soybean oil (including low linolenic soybean oil), coconut oil, cocoa butter, corn oil, peanut oil, cottonseed oil, canola oil (including high oleic canola oil), rapeseed oil (including high erucic rapeseed), sunflower oil (including high oleic sunflower oil), castor oil, safflower oil, linseed oil, tall oil, and the like. For instance, soybean oil may be used in its natural state, may be partially hydrogenated, may be fractionated, and/or may be used in some other state. Triacylglyceride stocks of animal origin, e.g., tallow, lard, chicken fat, and fish oil, may also be used as part or all of the precursor mixture.

The precursor mixture is preferably fully metathesized, but may be metathesized to other degrees while remaining within the scope of these exemplary embodiments.

The wax may include e from 1 to 100 wt. % of the metathesis-based product. According to some embodiments, the wax may contain at least about 10 wt. % of the metathesis product and may comprise at least about 15 wt. % or at least about 25 wt. % of the metathesis product. According to some embodiments, the wax may include identifiable amounts of components other than the metathesis product. These waxes may comprise no more than about 85 wt. % of the metathesis product and may sometimes include no more than about 50 wt. % or no more than about 40 wt. % or no more than about 20 wt. % of the metathesis product.

The wax may comprise a metathesis product such as a partially or fully hydrogenated metathesis product, which hydrogenated product may be present in the wax from about 1 to 100 wt. %. According to some embodiments, the wax may contain at least about 5 wt. % of the hydrogenated metathesis product and may comprise at least about 10 wt. % or at least about 15 wt. % of the hydrogenated metathesis product. According to some embodiments, the wax may include identifiable amounts of components other than the hydrogenated metathesis product. These waxes may comprise no more than about 85 wt. % of the hydrogenated metathesis product and may sometimes include no more than about 50 wt. % or no more than about 40 wt. % or no more than about 20 wt. % of the hydrogenated metathesis product.

A candle may be formed from a wax according to many exemplary embodiments. According to some embodiments a candle may be substantially composed of a metathesis product. According to other embodiments, a candle may include very little metathesis product. Waxes including a metathesis product or metathesis-like product may also include components other than the metathesis or metathesis-like portion. For instance, a wax may include a petroleum based wax component such as a paraffin component. The wax may also include a natural wax component; examples of such waxes including insect wax and plant wax. The wax may also contain non-waxy components such as free fatty acids, additives, etc. The additives may be used to add color or scent, give the wax insect repellency, improve a wax's compression moldability, inhibit migration of components, and/or perform any number of other useful functions and/or give the wax any number of useful properties.

The wax composition would preferably include at least about 51 wt. % of a component derived from renewable resources. More preferably, the wax composition would include at least about 70 wt. % of materials derived from renewable resources. In some instances, the wax composition include about 90 wt. % or more of materials derived from renewable resources In some embodiments, the candle wax may include at least about 10 wt. % of the metathesis or metathesis-like product. In some of these embodiments, the candle wax may comprise at least about 15 wt. % or at least about 20 wt. % or at least about 30 wt. % of the metathesis or metathesis-like product. In some embodiments, the candle wax may be substantially comprised of a metathesis or metathesis-like product (i.e. at least about 80 wt. %).

In some embodiments, the candle wax may include up to about 50 wt. % of the metathesis or metathesis-like product. In some of these embodiments, the candle wax may comprise up to about 40 wt. % or up to about 30 wt. % of the metathesis or metathesis-like product. In some embodiments, the candle wax may comprise no more than 20 wt. % of the metathesis or metathesis-like product.

In some embodiments, a candle wax may comprise up to about 50 wt. % mineral wax. In some of these embodiments, the candle wax may only comprise up to about 40 wt. % or up to about 30 wt. % of a mineral wax.

In some embodiments, the candle wax may comprise up to about 80 wt. % of a renewable resource based material that is not part of the metathesis product. In some embodiments, the candle wax may comprise up to about 60 wt. % or up to about 40 wt. % of a renewable resource based material that is not part of the metathesis product. In some embodiments, the wax may comprise substantially no renewable resource based material that is not part of the metathesis product (e.g. up to about 15 wt. %). The renewable resource based material may include or be substantially composed of a lipid-based material (or combination of lipid-based materials) such as vegetable oils and/or hydrogenated vegetable oils.

In some embodiments, the candle wax may comprise at least about 20 wt. % of a renewable resource based material that is not part of the metathesis product. In some embodiments, the candle wax may comprise at least about 30 wt. % or at least about 50 wt. % of a renewable resource based material that is not part of the metathesis product. In some embodiments, the candle wax may comprise substantially all renewable resource based material that is not part of the metathesis product (e.g. at least about 85 wt. %).

In some embodiments, a candle wax may comprise at least about 1 wt. % or at least about 5 wt. % free fatty acid. According to some embodiments, a candle wax may comprise no more than about 10 wt. % or no more than about 5 wt. % free fatty acid. In other embodiments, the candle wax may be substantially devoid of free fatty acid and may comprise no more than about 1 wt. % or, more desirably, no more than about 0.5 wt. % free fatty acid.

The candle waxes preferably have a melting point of at least about 45° C. and no more than about 75° C., but may have lower or higher melting points if desired. According to some embodiments, the candle wax may have a melting point of at least about 55° C. and generally no more than about 75° C., and sometimes at least about 56° C. and/or no more than about 60° C. or 65° C. According to other embodiments, the candle wax has a melting point generally in the range of about 50° C. to about 65° C., and sometimes of at least about 52° C. and/or no more than about 58° C. According to still other embodiments, the candle wax has a melting point of about 45° C. to about 60° C., and sometimes at least about 50° C. and/or no more than about 55° C.

The candle waxes may have Iodine Values (IV) of at least about 5 and no more than about 70. According to some embodiments, the candle wax may have an Iodine Value of at least about 10 or at least about 30. According to some of these embodiments, the candle wax may have an Iodine Value of at least about 40. According to some embodiments, the candle wax may have an Iodine Value up to about 55 or up to about 20. According to some of these embodiments, the candle wax may have an Iodine Value up to about 15. Some exemplary candle waxes may have Iodine Values of about 5 to about 20 or of about 10 to about 15. Other exemplary candle waxes may have an Iodine Value of about 30 to about 55 or about 40 to about 55.

Candle waxes according to these exemplary embodiments preferably include any number of characteristics. For instance, the glycerol-based portion of the wax preferably maintains a generally β' crystal structure when subjected to normal candle heating and cooling conditions.

Additionally, the candle wax or polyol wax component of the candle wax may include no more than about 5 to 15 wt. % 16:0 fatty acids in its fatty acid profile. The wax may also contain no more than 10 wt. % fatty acids having hydroxyl groups in its fatty acid profile. Further, the wax may contain no more than 25 wt. % fatty acids having no more than 16 carbon atoms or monobasic fatty acids having more than 18 carbon atoms in its fatty acid profile.

According to some embodiments, the wax may be designed to be slightly tackier. According to some of these embodiments, the wax may comprise at least about 1 wt. % or at least about 2 wt. % 18:2 fatty acids in its fatty acid profile. In some of these embodiments, the amount of 18:2 that is present, while meeting a minimum threshold, might still be limited. In this subset of such embodiments, the fatty-acid-based component of the wax may comprise up to about 15 wt. % or more typically about 3 to 10 wt. % 18:2 fatty acids in its fatty acid profile. According to some of these embodiments, the amount of 18:3 fatty acids in the fatty acid profile of the fatty-acid-based component maybe no more than about 0.5 wt. %.

According to some embodiments, the wax may be configured to be less sticky while still being capable of being molded by compression techniques. According to some of these embodiments, the fatty-acid-based component such a wax may comprise no more than about 5 wt. % 18:2 fatty acids in its fatty acid profile. According to some of these embodiments, the fatty-acid-based component of such a wax may comprise no more than about 2 wt. % 18:2 fatty acids in its fatty acid profile.

According to some embodiments, the wax may include a fatty-acid-based material and may comprise 15:0 fatty acids in the fatty acid profile of the fatty-acid-based material.

According to some embodiments, the wax may be designed to have a lower viscosity. According to some of these embodiments, the wax may comprise at least about 1 wt. % or at least about 2 wt. % 18:2 fatty acids in its fatty acid profile. In some of these embodiments, the amount of 18:2 that is present, while meeting a minimum threshold, might still be limited. In these subset of low viscosity embodiments, the wax may comprise up to about 20 wt. % or up to about 10 wt. % 18:2 fatty acids in its fatty acid profile. According to some of these embodiments, the wax may be limited to up to about 5 wt. % 18:2 fatty acids in its fatty acid profile.

According to some embodiments, the wax may be configured to be less sticky. According to some of these embodiments, the wax may comprise no more than about 5 wt. % 18:2 fatty acids in its fatty acid profile. According to some of these embodiments, the wax may comprise no more than about 2 wt. % 18:2 fatty acids in its fatty acid profile.

The candle wax can preferably pass a slump test, preferably passing it at at least 120° F.

Waxes suitable for use as pillar candles generally have a melting point of at least about 55° C. and generally no more than about 70° C., and may have a melting point of at least about 56° C. and/or no more than about 60° C. or 65° C. These waxes may have an IV of up to about 20 or up to about 15 or up to about 5. In some embodiments, the IV ranges from about 1 to 2. The wax may be in a particulate form, and the wax particles may be used to form the pillar candle by compression molding. A pillar candle may be over-dipped, or go through some other processes to attempt to give the candle an even appearance.

Waxes suitable for use in making votive candles have melting points generally in the range of about 50° C. to about 65° C., and may have melting points of at least about 52° C. and/or of no more than about 58° C. These waxes may have an IV of up to about 20 or up to about 15 or up to about 5. In some embodiments, the IV ranges from about 1 to 2. Some votive waxes may be required to pass a slump test. These waxes would preferably be able to pass a slump test at 120° F., but may also be acceptable if they pass at temperatures as low as about 115° F. or 117° F.

Waxes suitable for use as containers preferably have a melting point of about 45° C. to about 60° C. In some embodiments, they may have melting points of at least about 50° C. and/or no more than about 55° C. These waxes may have an IV of up to about 80 or up to about 55 and may have an IV of at least about 30 or at least about 40. These waxes, like waxes suitable for use as Votive candle waxes, would preferably be able to pass a slump test at 120° F., but may also be acceptable if they pass at temperatures as low as about 115° F. or 117° F.

There are likely some waxes which may be acceptable for use as both votive and pillar waxes. Also, there are likely some waxes which may be acceptable for use as both votive and container waxes. While generally less common, there may be some waxes that are suitable for use as both pillar and container waxes as well.

Candles formed from the waxes generally include a wick in addition to the wax. The wick can be made of any number of materials, but are preferably a natural wick such as a braided cotton wick.

Formation of Candles

Candles can be produced from the polyol-ester-based material using a number of different methods. In one common process, the polyol-ester-based wax is heated to a molten state. If other additives such as colorants and/or fragrance oils are to be included in the candle formulation, these may be added to the molten wax or mixed with polyol-ester-based wax prior to heating. The molten wax is then solidified around a wick. For example, the molten wax can be poured into a mold which includes a wick disposed therein. The molten wax is then cooled to solidify the wax in the shape of the mold. Depending on the type of candle being produced, the candle may be unmolded or used as a candle while still in the mold. Where the candle is designed to be used in unmolded form, it may also be coated with an outer layer of higher melting point material.

Alternatively, the polyol-ester-based material can be formed into a desired shape, e.g., by pouring molten polyol-ester-based wax into a mold and removing the shaped material from the mold after it has solidified. A wick may be inserted into the shaped waxy material using techniques known to those skilled in the art, e.g., using a wicking machine such as a Kurschner wicking machine.

Polyol-ester-based waxes can also be formed into candles using compression molding techniques. This process often involves forming the wax into a particulate form and then introducing the particulate wax into a compression mold.

The candle wax may be fashioned into a variety of particulate forms, commonly ranging in size from powdered or ground wax particles approximately one-tenth of a millimeter in length or diameter to chips, flakes or other pieces of wax approximately two centimeters in length or diameter. Where designed for use in compression molding of candles, the waxy particles are generally spherical, prilled granules having an average mean diameter no greater than one (1) millimeter.

Prilled waxy particles may be formed conventionally, by first melting a triacylglyceride-based material, in a vat or similar vessel and then spraying the molten waxy material through a nozzle into a cooling chamber. The finely dispersed liquid solidifies as it falls through the relatively cooler air in the chamber and forms the prilled granules that, to the naked eye, appear to be spheroids about the size of grains of sand. Once formed, the prilled triacylglyceride-based material can be deposited in a container and, optionally, combined with the coloring agent and/or scenting agent.

Particulates, including prilled waxy particles, can be formed into candles using compression techniques. The particulates can be introduced into a mold using a gravity flow tank. The mold is typically a bronze or teflon mold. A physical press then applies between 1000 and 2000 pounds of pressure at the ambient room temperature (generally 65 to 85° F.). The pressure can be applied from the top or the bottom. The formed candle can then be pushed out of the mold. A candle formed by this method may not tend to have even appearing sides. A candle may experience some heat (below the melting point of the candle) when run through the extruder, which heat will tend to glaze over the side and remove some of the uneven appearance. If desired, a candle formed by this method may be over-dipped in hot liquid wax to give the outer surface of the candle a smoother appearance.

Equipment and procedures for wax powder compression are described in publications such as "Powder Compression Of Candles" by M. Kheidr (International Group Inc., 1990), incorporated by reference. Compression-molding can be conducted under conditions comprising a mold pressure between about 1000-4000 psi, a compression time between about 1-20 seconds, and a prilled wax temperature between about 15° C. to about 25° C.

The particle size distribution specification of a prilled wax composition may be important for achieving a superior combination of properties in the final candle product. The specified particle size distribution permits the prilled wax composition to have a powder density between about 0.55-0.65 grams per centimeter, and subsequently allows the compression-molded candle product to have a density between about 0.8-0.9 gram per cubic centimeter.

Additionally, the particle size distribution specification of a prilled wax composition contributes other important property improvements to the final candle product. A high degree of particle fusion is effected by the compression-molding procedure, and the final candle product is characterized by desirable hardness and strength properties, and by a high gloss or satin candle surface finish.

A candle may also be formed from a candle wax according to various embodiments by extrusion molding the wax to form the candle. In this type of method for forming a candle, a machine generally pushes wax out through a shaped template. The wax is typically introduced into the extruder in prilled form. The wax may be maintained in a viscous state during the extrusion process and is then cooled after extrusion to harden the wax. Once extruded, the long wax sections which are typically produced may be sliced into desired lengths.

The present waxes can also incorporate between about 0.1-5 weight percent of a wax fusion enhancing type of additive in the prilled wax composition which is being subjected to a compression molding procedure. Suitable wax-fusion enhancer additives include benzyl benzoate, dimethyl phthalate, dimethyl adipate, isobornyl acetate, cellusolve acetate, glucose pentaacetate, pentaerythritol tetraacetate, trimethyl-s-trioxane and N-methyl pyrrolidone. The prill composition additive may also have a beneficial effect on the combustion properties of a candle product which is compression molded.

When waxes are placed in molds to form candles, the waxes preferably have good mold release. To have 'good mold release', the wax preferably contracts enough to leave $\frac{1}{16}^{th}$ of an inch between the formed candle and the mold. Good mold release, as a property of a candle wax, is defined by the amount of contraction in the molded wax at a given area (which can be defined by width and length, by diameter, etc). A candle would preferably have good mold release for candles having a diameter of about 1.5 to about 3.5 inches and candles having diameters of about 4 inches to about 7 inches. The area by which mold release is defined is based on the particular application.

A candle may also be formed from a candle wax according to various embodiments by extrusion molding the wax to form the candle. In this type of method for forming a candle, a machine generally pushes wax out through a shaped template. The wax is maintained in a viscous state prior to extrusion and is quickly cooled after extrusion to harden the wax. Once extruded, these long wax sections are sliced into their proper lengths.

The basic techniques that can be used to form candles, can also be used to form other wax-based structures such as crayons, fire logs, tarts, billets, sheets, and profiles. A tart is a wax article with a high fragrance content that is used to deliver fragrance by heating indirectly and melting. Tarts may be manufactured by methods similar to candle manufacturing, for example, pouring a molten formulation into a mold, extrusion, and compression molding. Compositions of tarts are similar to those compositions used in candles. Further, various other methods for forming wax-based articles may be used to form candles including, but not limited to, casting, injection molding, cold forming, vacuum forming, blow molding, transfer molding, etc.

Bleaching, Distilling, and Deodorizing

The polyol-ester-based wax may also be bleached and deodorized. Bleaching can be done using diatomaceous earth which is acid activated and added under vacuum. This tends to remove soaps from the wax. Also, the polyol-ester-based wax can be deodorized by removing free fatty acids. This can be done by distilling the free fatty acids at 450° F. to 500° F. The polyol based ester may also be subject to other processing and/or purifying steps.

In some embodiments, the metathesis product is distilled in order to remove or reduce hydrocarbon impurities. For example, the metathesis product may be distilled in order to remove or reduce hydrocarbons having a molecular weight of about 200 gram/mole or less or to remove or reduce hydrocarbons having a molecular weight of about 300 grams/mole or less. In some embodiments, the resulting composition comprises about 1 wt. % or less of the hydrocarbons. In other embodiments, the resulting composition comprises about 0.1 wt. % or less of the hydrocarbons. In some embodiments, the composition comprises less than about 0.1 wt. % hydrocarbons. The composition may be prepared by a process comprising the steps of: (a) providing a polyol fatty acid ester having a fatty acid composition that includes at least one unsaturated fatty acid; (b) metathesizing the polyol fatty acid ester in the presence of a metathesis catalyst to produce a metathesis product comprising hydrocarbons, triacylglycerides, and triacylglyceride metathesis oligomers; and (c) distilling the metathesis product to remove at least a portion of the hydrocarbons. The distilling step may be conducted, for example, by steam stripping the composition. Distilling may be accomplished by sparging the mixture in a vessel, typically agitated, by contacting the mixture with a gaseous stream in a column that may contain typical distillation packing (e.g., random or structured), or evaporating the lights in an evaporator such as a wiped film evaporator. Typically, steam stripping will be conducted at reduced pressure and at temperatures ranging from about 100° C. to 250° C. The temperature may depend, for example, on the level of vacuum used, with higher vacuum allowing for a lower temperature and allowing for a more efficient and complete separation of volatiles.

The following examples are presented to illustrate the present invention and to assist one of ordinary skill in making and using the same. The examples are not intended in any way to otherwise limit the scope of the invention.

EXAMPLES

Unless otherwise specified herein (e.g., in the case of the relative amounts of TAGs versus oligomers in the metathesis products), all percentages listed herein are shown in wt. %.

Polymers by High Performance Size Exclusion Chromatography Coupled to Evaporative Light Scattering Detection (HPSEC/ELSD).

Liquid chromatography (LC) using a Waters 2795 liquid chromatograph coupled to an Evaporative Light Scattering Detector (ELSD) was used in the separation of polymers. Samples were prepared at 5 mg/mL and were separated with two PLgel, 3 μm, 100 A, 300×7.5 mm columns. The column temperature was 50° C. A higher temperature was needed to elute the metathesized samples from the columns. The mobile phase was THF at a flow rate of 1.0 mL/min. The injection volume was 20 μL, and the run time was 20 min. The ELSD settings were 50° C., Gain=6, and Nitrogen=3.5 bar (50 psi). No response factors were developed. Data is presented as area percent.

Fatty Acid Composition and Oil Content by Direct Extraction Method (DEM) and Gas Chromatography Coupled to Flame Ionization Detection (GC/FID).

The DEM utilizes a simultaneous alkaline saponification (NaOH/MeOH), extraction (organic solvent) and derivatization ($BF_3$/MeOH) reaction. Approximately 100 mg of sample was used. An organic solvent (heptane) containing an internal standard (IS, tritridecanoin, C39 TAG) is added to the sample, and then the saponification reagent is added. Lipid is saponified and extracted from the sample with the organic solvent, and all components with esterified fatty acids are converted into free fatty acids (FFAs) salts. $BF_3$ is the catalyst and McOH is present to form the methyl esters. Saturated sodium chloride is added to partition the methyl esters into the organic layer. The methyl esters are analyzed by gas chromatography (GC) on a very polar stationary phase (CP-Sil 88, 100 m×0.25 mm×0.20 μm) coupled to a flame ionization detector (FID). The temperature program was 170° C. (40 min) to 190° C. at 20° C./min to 215° C. at 8° C./min (25 min). Hydrogen was the carrier gas, and inlet pressure was 20.8 psi in the constant flow mode (g=26 cm/s). The injector and detector temperatures were 250° C. The split ratio was approximately 100:1. Oil and fatty acid contents were determined according to the Nutritional Labeling and Education Act of 1990 (AOAC 996.06), and were based on TAG and fatty acid weight percent basis, respectively.

Hydrocarbons by Lipid Profile.

This method was used to determine a wide range of components via a single technique. The samples are not saponified nor hydrolyzed before derivatization allowing for differentiation between components with vastly differing boiling points, such as free fatty acids (FFAs) to triacylglycerides (TAGs). The components detected cover a range of boiling points (110° to 340° C.). The samples (50 mg) were silylated with N,O,-bis-(trimethylsilyl)trifluoroacetamide (BSTFA) containing 1% trimethylchlorosilane and pyridine. An internal standard (IS) of heptadecanyl stearate (HDS) was used at 10 mg. Samples were diluted 1:200 with toluene. The trimethylsilane (TMS) ethers were analyzed by cool on-column (COC) gas chromatography (GC) with a non-polar column stationary phase (DB-5HT, 15 m×0.25 mm×0.10 μm) coupled to a flame ionization detector (FID). The temperature program was 110° C. (0.2 min) to 140° C. at 30° C./min to 340° C. at 10° C./min (10 min). Hydrogen was the carrier gas, and inlet pressure was 6.7 psi at 110° C. in the constant flow mode. The detector temperature was 370° C. Calibration curves were developed for the following classes of compounds: glycerol, fatty acid methyl esters (FAMEs), fatty acid ethyl esters (FAEEs), FFAs, hydrocarbons (HCs), monoacylglycerols (MAGs), diacylglycerols (DAGs), TAGs, sterols, steryl esters (SEs), tocopherol acetate, squalene, and tocopherols.

General Procedure 1:

An oil is self-metathesized in the presence of ruthenium catalyst. The self-metathesized oil is then sent to either of the two possible catalyst removal steps (filtration or water/methanol wash). The purified self-metathesized oil is then hydrogenated in the presence of Ni catalyst. The Ni catalyst is then removed by filtration to give the final wax product.

In a 50-gallon batch, the oil is degassed overnight (~16 hrs) with argon or nitrogen at an estimated rate of 10 mL/min. Degassing the oil tends to help prevent metathesis catalyst decomposition. The oil is then heated to 70° C. Ruthenium catalyst (C827) is added at 50 ppm. The reaction is run for 2 hours at 1 atm. The stir rate was not measured, but stirring was sufficient to cause a small amount of splash from the baffle. The mixture should be virtually non-volatile at 70° C., aside from possible formation of minute amounts of 3-hexene and 1,4-cyclohexadiene.

The catalyst is removed using tris-(hydroxymethyl)phosphine ("THMP") which is prepared by adding 245 g of tetrakis-(hydroxymethyl)phosphonium chloride (1.03 mol, Strem) and 500 mL of isopropyl alcohol (IPA) to a 2 L round-bottomed flask, degassing the mixture with nitrogen for 20 minutes, slowly adding 64 g (1.03 mol, 90% purity, Aldrich) of potassium hydroxide over 30 minutes to the vigorously stirring solution, while under a nitrogen atmosphere, and, after the potassium hydroxide has been added, stirring the reaction for an additional 30 minutes. This reaction is exothermic, and produces THMP, formaldehyde, potassium chloride, and water. The catalyst is then removed using the THMP by adding 25-100 mol equivalents of THMP per mole of ruthenium catalyst, stirring vigorously at 60-70° C. for 18 to 24 hours, under nitrogen, adding degassed water or methanol (~150 mL/L of reaction mixture) and vigorously stirring for 10 minutes, and centrifuging the mixture for phase separation. The oil may have to be heated to remove the residual water or methanol. The aqueous phase will contain small amounts of IPA, formaldehyde, and potassium chloride, and will need to be purged or cleaned for recycling.

The metathesis product can then be hydrogenated by heating the self-metathesized oil to 350° F., while held under nitrogen, adding 0.4 wt % Ni catalyst to the oil once at 350° F., starting the flow of hydrogen at a pressure of 35 psi, having a hold temperature of about 410° F., and checking the reaction at 1 hour to see where the IV is in comparison to target. A 2.5 kg batch may take about 30-45 minutes. After about 2 hours (oil should be fully hydrogenated), nitrogen is put back in the vessel and the oil is cooled. The hydrogenated self-metathesized oil may then be filtered to remove catalyst.

Example 1

Three sample metathesis products (A, C, and E) were subject to the metathesis reaction described in General Procedure 1 to different degrees. These three metathesis products were hydrogenated according to General Procedure 1 to form hydrogenated versions of the metathesis products (B, D, and F).

Sample A was created starting with unrefined soybean oil and 100 ppm of catalyst C627. The reaction was run at room temperature for 20 hrs and then warmed to 40 C for 5 hrs. Sample C was created using unrefined soybean oil and 50 ppm of catalyst C627. The reaction was run at room temperature for 22 hrs. Sample E was created using unrefined soybean oil and 50 ppm of catalyst C715. Catalyst C715 is the same as catalyst C627 except that it has bromide ligands in place of the chloride ligands. The reaction was run at room temperature for 22 hrs.

Polymer analysis indicated that each of the metathesized samples and their corresponding hydrogenated samples (in parentheses) A (B), C (D), and E (F) were reacted to different endpoints. As can be seen in Table 1, sample C was the least reacted (most triacylglyceride-TAG-remaining) and sample A was the most reacted (lowest triacylglyceride and highest oligomer concentration). HPSEC analysis indicated sample B had 21.2% unreacted triacylglyceride, sample D had 93.3% unreacted triacylglyceride, and sample F had 80.8% unreacted triacylglyceride. Samples A, C, and E had similar HPSEC chromatograms as their corresponding hydrogenated samples. The relative amounts are in area % as described in the Experimental section above.

TABLE 1

Wax Compositions

| | A | B | C | D | E | F |
|---|---|---|---|---|---|---|
| Total Oligomers | 75.6 | 78.7 | 6.9 | 6.7 | 20.5 | 19.3 |
| Tetramers and Higher Oligomers | 46.1 | 50.7 | ND | ND | 0.5 | 0.4 |
| Dimers | 16.4 | 16.1 | 6.5 | 6.4 | 16.5 | 15.9 |
| Trimers | 13.0 | 12.0 | 0.4 | 0.3 | 3.5 | 3.0 |
| TAG | 24.4 | 21.2 | 93.1 | 93.3 | 79.6 | 80.8 |

Table 2 shows the fatty acid composition of the six samples. The oil content is determined by converting the fatty acid methyl esters (FAME) into their triacylglyceride equivalents basis the use of an internal standard, so the values are on a weight percent basis. All the individual fatty acids were determined by converting the FAME into fatty acid (FA) equivalents and are on a weight basis.

TABLE 2

Fatty Acid Compositions of Wax Compositions

| | A | B | C | D | E | F |
|---|---|---|---|---|---|---|
| Trans | 13.35 | 1.36 | 8.02 | 0.01 | 11.49 | 1.65 |
| C18:1 (% w/w FA) | 8.06 | 1.87 | 20.13 | 0.11 | 17.86 | 2.21 |
| C18:2 (% w/w FA) | 8.81 | 0.58 | 41.64 | ND | 31.78 | 0.27 |
| C18:3 (% w/w FA) | 0.12 | 0.01 | 4.01 | ND | 2.26 | 0.01 |
| C18:0 (% w/w FA) | 4.03 | 18.51 | 4.11 | 68.12 | 4.06 | 50.38 |
| Saturated FA (% w/w FA) | 17.17 | 44.69 | 15.50 | 83.2 | 15.59 | 67.40 |
| C12:0 (% w/w) | 0.02 | 1.17 | 0.01 | 0.29 | 0.02 | 0.50 |
| C15:0 (% w/w) | 0.04 | 10.70 | 0.03 | 2.73 | 0.03 | 4.55 |

Example 2

Samples G and I were created in a manner similar to sample A starting with refined bleached soybean oil. Sample G was created using 100 ppm of catalyst C627 running at room temperature for 18 hrs. Sample I was created using 100 ppm of catalyst C627 running at room temperature for 19 hrs. Samples G and I were hydrogenated to form samples H and J, respectively. Some results of the analysis are included below, although there is a potential that an unidentified substance is present upon hydrogenation of the material which appears at the same point where conjugated linoleic acid appears during the analysis and/or causes the apparent amount of total oligomers (particularly the tetramer and higher order oligomer) to appear as if they changed during hydrogenation.

Table 3 and 4 show fatty acid and oligomer analysis of samples G-J. The relative amounts of oligomers are in area % as described in the Experimental section above.

TABLE 3

Fatty Acid Compositions of Wax Compositions

|  | G | H | I | J |
|---|---|---|---|---|
| Trans (% w/w FA) | 12.26 | 1.30 | 19.66 | 2.46 |
| C18:1 (% w/w FA) | 6.41 | 1.57 | 13.63 | 2.16 |
| C18:2 (% w/w FA) | 7.12 | 16.66 | 9.77 | 17.86 |
| CLA Retention Time** (% w/w FA) | 0.35 | 16.58 | 2.80 | 17.14 |
| C18:3 (% w/w FA) | 0.31 | 0.03 | 0.34 | 0.04 |
| C16:0 (% w/w FA) | 10.69 | 12.56 | 10.23 | 11.42 |
| C18:0 (% w/w FA) | 4.24 | 16.62 | 4.29 | 16.80 |
| Saturated FA (% w/w FA) | 18.62 | 45.74 | 18.22 | 44.23 |
| C12:0 (% w/w) | 0.02 | 1.37 | 0.02 | 1.22 |
| C15:0 (% w/w) | 0.01 | 11.85 | 0.02 | 11.28 |

TABLE 4

Wax Compositions

|  | G | H | I | J |
|---|---|---|---|---|
| Total Oligomers | 83.7 | 70.2 | 82.1 | 71.4 |
| Tetramers and Higher Oligomers | 67.7 | 46.6 | 55.1 | 48.7 |
| Dimers | 12.7 | 12.2 | 14.1 | 12.5 |
| Trimers | 13.3 | 11.4 | 12.9 | 10.2 |
| TAG | 16.3 | 29.7 | 17.9 | 28.2 |

Example 3

Table 5 shows Hydrocarbon (HC), polymer, and C6 to C15 fatty acid content comparisons of hydrogenated metathesis products B, D, F, H, and J. The relative amounts of polymers (as opposed to TAGs) are in area % as described in the Experimental section above.

TABLE 5

Properties of Wax Compositions

|  | B | D | F | H | J |
|---|---|---|---|---|---|
| HC | 9.10 | 1.78 | 3.58 | 1.69 | 6.10 |
| C6-C15 FA | 22.86 | 5.97 | 10.03 | 23.34 | 2.93 |
| Polymer | 78.7 | 6.70 | 19.3 | 70.2 | 71.4 |

Example 4

Waxes which may be suitable for use as candles, particularly pillar and votive candles, were formed using metathesis products formed from soybean oil. The metathesis products were formed under conditions similar to those described for metathesis product B of Example 2, except that refined bleached soybean oil was used as a starting product. The metathesis products had characteristics similar to that of product B of Example 2. The metathesis products were combined with one or more of a soybean oil hydrogenated to an IV of no more than about 5 ("FH-SBO"), a soybean oil hydrogenated to an IV of about 65, a soybean oil hydrogenated to an IV of about 90, a paraffin wax, and/or free stearic acid. The components that make up the resulting wax can be heated to 170° F. (circa 77° C.) and stirred to thoroughly blend the components. Table 6 shows some compositions of exemplary waxes.

TABLE 6

Compressed Pillar/Votive Formulas

|  | FH—SBO | Met. Wax J | Met. Wax H | 65 IV Soy | 90 IV Soy | Paraffin (p) or Beeswax (b) | Free Stearic Acid | Melting Point (° F.) | Iodine Value |
|---|---|---|---|---|---|---|---|---|---|
| Blend 5-1 | 45 | 30 | 0 | 25 | 0 | 0 | 0 | 136 | 17 |
| Blend 5-2 | 45 | 35 | 0 | 20 | 0 | 0 | 0 | 136.7 | 12.4 |
| Blend 5-3 | 40 | 35 | 0 | 20 | 0 | 0 | 5 | 136.2 | 12.2 |
| Blend 5-4 | 35 | 35 | 0 | 20 | 0 | 0 | 10 | 135.4 | 11.9 |
| Blend 5-5 | 27 | 0 | 21 | 12 | 0 | 40 p | 0 | 143.2 | 9.2 |
| Blend 5-6 | 31 | 0 | 21 | 8 | 0 | 40 p | 0 | 145.3 | 6.8 |
| Blend 5-7 | 27 | 0 | 21 | 0 | 12 | 40 p | 0 | 143.2 | 12.6 |
| Blend 5-8 | 21 | 0 | 21 | 0 | 18 | 40 p | 0 | 144.1 | 17.8 |
| Blend 5-9 | 21 | 0 | 21 | 0 | 15 | 40 p | 3 | 139.5 | 15.2 |
| Blend 5-10 | 29 | 0 | 21 | 0 | 10 | 40 p | 0 | 145.1 | 10.8 |
| Blend 5-11 | 24.2 | 0 | 17.5 | 0 | 8.3 | 50 p | 0 | 145.5 | 9.4 |
| Blend 5-12 | 33.8 | 0 | 24.5 | 0 | 11.7 | 30 p | 0 | 143.3 | 12.3 |
| Blend 5-13 | 34 | 0 | 21 | 0 | 5 | 40 p | 0 | ND | ND |
| Blend 5-14 | 40 | 20* | 0 | 0 | 0 | 40 p | 0 | 145 | <5 |
| Blend 5-15 | 65 | 35* | 0 | 0 | 0 | 0 | 0 | 139.4 | <5 |
| Blend 5-16 | 40 | 20* | 0 | 0 | 0 | 40 b | 0 | 143 |  |
| Blend 5-17 | 53.6 | 26.4* | 0 | 0 | 0 | 20 b | 0 | 138 |  |

*Different lots of fully hydrogenated, metathesized soybean oil with similar characteristics were used to form these blends.

The 90 IV soybean oil in the formulations shown in Table 6 (and in Table 7 below) could be replaced in any of the formulas by Refined Bleached and Deodorized (RBD) soybean oil.

Example 5

Waxes which may be suitable for use in candles, particularly container or votive candles, were formed using the metathesis product of Example 1. The metathesis products was combined with one or more of a soy oil hydrogenated to an IV of about 0, a soy oil hydrogenated to an IV of about 65, a soy oil hydrogenated to an IV of about 90, and free stearic fatty acid. The components that make up the resulting wax can be heated to 170° F. (circa 77° C.) and stirred to thoroughly blend the components. Table 7 shows some examples of some exemplary waxes.

TABLE 7

Container Formulas

|  | 0 IV Soy | Metathesis Wax H | Metathesis Wax J | 65 IV Soy | 90 IV Soy | Free Stearic Acid | Melting Point (° F.) | Iodine Value |
|---|---|---|---|---|---|---|---|---|
| Blend 6-1 | 0 | 100 |  | 0 | 0 | 0 | 127.4 | 1.8 |
| Blend 6-2 | 13.5 | 10 |  | 76.5 | 0 | 0 | 127.3 | 47.9 |
| Blend 6-3 | 14.8 | 1 |  | 84.2 | 0 | 0 | 132.1 | 52.5 |
| Blend 6-4 | 14.7 | 2 |  | 83.3 | 0 | 0 | 131.4 | 51.9 |
| Blend 6-5 | 14.4 | 3 |  | 81.6 | 0 | 0 | 131.1 | 50.9 |
| Blend 6-6 | 14.2 | 5 |  | 80.8 | 0 | 0 | 130.6 | 50.5 |
| Blend 6-7 | 8.5 | 10 |  | 76.5 | 0 | 5 | 127.5 | 47.5 |
| Blend 6-8 | 0 |  | 85 | 0 | 10 | 5 | 125.3 | 10.5 |
| Blend 6-9 | 27.5 |  | 35 | 0 | 32.5 | 5 | 126.9 | 30.6 |
| Blend 6-10 | 12 |  | 10 | 68 | 10 | 0 | 128.2 | 51.6 |

Example 6

Metathesis and hydrogenation of used restaurant frying oil was carried out as follows. Used fryer oil was placed in a 600 ml Parr reactor and purged with argon for a minimum of 4 hours. Ruthenium catalyst (Materia, Inc.) was added and the reaction mixture heated to 70° C. and reaction temperature maintained for 3 hours. Nickel catalyst (Johnson Matthey Catalysts) is added to reactor and purged 3 times with nitrogen. The relative amounts of catalysts employed is shown below. The reactor was then purged 2 times with hydrogen. The reactor was pressurized to 50 psi with hydrogen and heated to 190° C. When desired reaction temperature is reached, hydrogen pressure was increased to 100 psi. Temperature and pressure were maintained for 2 hours.

| Used restaurant fryer oil | 100% w/w |
|---|---|
| C827 ruthenium catalyst | 0.05% w/w |
| Pricat 9920 nickel catalyst | 0.02% w/w |

At end of reaction, pressure is relieved and the reactor is cooled to <80° C. and oil is filtered through fine filter paper to remove catalyst. After cooling to room temperature, the oil is a white waxy solid. The final oil had an iodine value of 50 compared to the initial used fryer oil which had an iodine value of 107.

Example 7

A number of oils were subjected to metathesis under the standard conditions that were used to produce a metathesis product from soybean oil (see General Procedure 1) with a metathesis catalyst loading of 500 ppm. The resulting metathesis products were then hydrogenated according to the procedures described in Examples 8 to 13. Some of the characteristics of the hydrogenated metathesis products are summarized in Table 8 below.

TABLE 8

Hydrogenated Metathesized Oils

| Starting Oil | Iodine Value | Melt Pt. (° C.) |
|---|---|---|
| Canola | 14 | 50.3 |
| Soybean** | 2 | 53 |
| Linseed | 5.2 | 49.4 |
| Palm | 0.65 | 53.4 |

TABLE 8-continued

Hydrogenated Metathesized Oils

| Starting Oil | Iodine Value | Melt Pt. (° C.) |
|---|---|---|
| Tallow | 0.46 | 56.3 |
| Fish | 2.5 | 42.8 |
| Castor | 28 | 48.5 |
| Used Fryer Oil | 50 | — |

**Metathesis Wax H

Example 8

Metathesized canola oil (299.5 grams) was placed in a 600 ml stainless steel Parr pressure reactor along with Nickel catalyst (1.26 grams, Pricat 9920, Unichema International). The Parr reactor was sealed and purged 5 times with nitrogen. It was then heated to 190° C. before the vessel was pressurized to at least 100 psi with hydrogen gas. The contents were then stirred at 700 rpm at 190° C. for 3.0 hours, while maintaining the 100 psi of hydrogen pressure. Afterward the Parr was cooled to around 120° C., opened, and the hydrogenated oil vacuum filtered through fine filter paper to remove the catalyst. The final product was titrated for iodine value (IV) to determine the extent of hydrogenation. The resulting product had an Iodine Value of 14, a melting point of 50.3° C., and was an off-white waxy solid.

Example 9

Metathesized castor oil (300.2 grams) was mixed with Nickel catalyst (5.66 grams, Pricat 9920) and hydrogenated as described above at 190° C. under 100 psi of hydrogen gas for 2.0 hours. The resulting product had an Iodine Value of 28, a melting point of 48.5° C., and was a gray/black waxy solid.

Example 10

The hydrogenation of metathesized fish oil was done in two steps. The first hydrogenation was done with metathesized fish oil (261.3 grams) mixed with Nickel catalyst (1.07 grams, Pricat 9920) at 190° C. under 100 psi of hydrogen gas for 6.0 hours. The resulting product was still a liquid. The mixture was subjected to a second hydrogenation using the same mass of oil mixed with additional nickel catalyst (11.02 grams), at 200° C. under 100 psi of hydrogen gas for another 4 hours. The product after the second hydrogenation was a soft, off-white, waxy solid with an IV of 2.5 and a melting point of 42.8° C.

Example 11

The hydrogenation of metathesized linseed oil was done in two parts. The first hydrogenation was done with metathesized linseed oil (299.6 grams) mixed with Nickel catalyst (1.27 grams, Pricat 9920), at 190° C. under 100 psi of hydrogen gas for 3.0 hours. The resulting product was still a liquid. The mixture was subjected to a second hydrogenation using 218.6 grams of the oil from the first hydrogenation, with additional nickel catalyst (11.00 grams, Pricat 9920), at 190° C. under 100 psi of hydrogen gas for another 2.0 hours. The product after the second hydrogenation was an off-white solid with an IV of 5.2 and a melting point of 49.4° C.

Example 12

Metathesized palm oil (302.5 grams) was mixed with Nickel catalyst (1.49 grams, Pricat 9920) and stirred at 200° C. under 500 psi of hydrogen gas for 2.0 hours. The resulting product had an Iodine Value of 0.65, a melting point of 53.4° C., and was an almost paper-white waxy solid.

Example 13

Metathesized tallow (300.7 grams) was mixed with Nickel catalyst (1.54 grams, Pricat 9920) and stirred at 200° C. under 500 psi of hydrogen gas for 2.0 hours. The resulting product had an Iodine Value of 0.46, a melting point of 56.3° C., and was a paper-white waxy solid.

Example 14

RBD soybean oil (~780 kg) was charged to an agitated 2600L vessel. The vessel and soybean oil were then sparged with Ar gas overnight. The soybean oil was then heated to a temperature of 70 C and 39 grams (50 ppm) of C827 ruthenium metathesis catalyst was added to the soybean oil to initiate the metathesis reaction. The agitated vessel was operated with a slight head pressure (~0.2 psig) of Ar gas. The metathesis reaction was allowed to proceed for two hours. Following this, the metathesized oil was held in the vessel for an additional 4-5 hours. Following this, the metathesized oil was transferred to an agitated holding tank in preparation for hydrogenation. The metathesized oil was then split into four approximately equal batches for hydrogenation in order to accommodate the 300L agitated, pressure-rated vessel that was available. A loading of 0.4 wt % Ni hydrogenation catalyst (Pricat 9925, from Johnson Matthey) was used for all batches. The reaction conditions for the four hydrogenation batches are summarized in Table 9.

TABLE 9

| batch | Batch size | Temperature | $H_2$ pressure | Reaction time |
| --- | --- | --- | --- | --- |
| 1 | 194 kg | 210° C. | 50 psig | 4.0 hr |
| 2 | 193 kg | 175° C. | 90 psig | 4.0 hr |
| 3 | 193 kg | 185° C. | 90 psig | 2.3 hr |
| 4 | 180 kg | 185° C. | 90 psig | 2.7 hr |

The four hydrogenation products were combined in the 2600L agitated tank in advance of filtration. The combined hydrogenated metathesized oil was held at 70° C. Citric acid (0.1 wt %), bleaching clay (2.0 wt %), and filter aid (0.1 wt %) were mixed with the oil before passing through a plate and frame filter (4×2" frames). A second pass was required due to breakage of one of the filter papers in the first pass. After filtration, 675 kg of hydrogenated metathesized soybean oil was recovered.

Example 15

18,300 pounds of RBD soybean oil (Cargill) was transferred from a tank into a nitrogen purged reaction vessel. Separately, 415 grams (50 ppm catalyst for the final reaction mixture) of C827 metathesis catalyst was slurried in about 4 gallons of soybean oil. The resulting slurry was added to the soybean oil in the reaction vessel which was held at a temperature of 70° C. The reaction mixture was then held in the reaction vessel for a period of about 3 hours. GC analysis of samples of the reaction mixture showed that the reaction mixture reached equilibrium about 30 minutes after addition of the metathesis catalyst.

Next, 27.5 pounds (12.5 kg) of hydrogenation catalyst (PRICAT 9925 from Johnson Matthey) was charged to the vessel. Following addition of the catalyst, the head space in the vessel was charged with $H_2$ gas. During this time, the reaction mixture was heated to 120° C. When the temperature reached 120° C., the $H_2$ gas in the head space was increased to a pressure of 50 psig. The heat of the exothermic reaction was used to raise the temperature of the reaction mixture to 185° C. $H_2$ charging continued for an additional 3 hours. The final IV for the metathesized soybean oil was less than 1.

In the same reaction vessel a steady sparge of steam was introduced to remove the more volatile components by steam stripping. The vessel was cooled during stripping to 120° C. The resulting product was filtered at 120° C. by recirculating the product through a plate and frame filter (Sparkler, Conroe, Tex.) with a pre-coat of about 25 pounds of diatomaceous earth filter aid ("CELATOM FW-14" from EaglePicher Filtration, Reno, Nev.). The final Ru content was less than 0.07 ppm Ru.

Example 16

15,900 pounds of RBD soybean oil (Cargill) was loaded into a reaction vessel. The soybean oil was agitated and was sparged with $N_2$ gas for 2.5 hours at a rate of 50 SCFH. Separately, 361 grams (50 ppm of catalyst in the final reaction mixture) of C827 metathesis catalyst was slurried in about 3 gallons of soybean oil. The resulting slurry was added to the soybean oil in the reaction vessel. Following addition of the catalyst, the head space in the vessel was evacuated and purged with $N_2$ gas a total of 3 times over a period of 1 hour. During this time, the reaction mixture was heated to 71° C. The reaction mixture was then held in the reaction vessel for a period of about 3 hours during which the temperature rose to 76° C. GC analysis of samples of the reaction mixture showed that the reaction mixture reached equilibrium about 30 minutes after addition of the metathesis catalyst.

Next, 35.0 pounds (15.9 kg) of hydrogenation catalyst (PRICAT 9925 from Johnson Matthey) was charged to the vessel. Following addition of the catalyst, the head space in the vessel was evacuated and purged with $N_2$ gas a total of 3 times over a period of 1 hour. During this time, the reaction mixture was heated to 130° C. When the temperature reached 130° C., $H_2$ gas was charged to the vessel. Thirty minutes into hydrogenation the reaction mixture reached a temperature of 180° C. and the flow of hydrogen was stopped for a period of about 75 minutes. After this, the $H_2$ charging resumed for an additional 3 hours during which the temperature ranged between 172° C. and 194° C. The resulting hydrogenated metathesized soybean oil was cooled to a temperature of 84° C. and excess $H_2$ was vented off. The oil was held at about 5 to 8 prig for about 9.5 hours before filtering.

The resulting product was filtered by recirculating the product through a plate and frame filter (Sparker, Conroe, Tex.) with a pre-coat of about 25 pounds of diatomaceous earth filter aid ("CELATOM FW-14" from EaglePicher Filtration, Reno, Nev.). The product was recirculated through the filter for about 13 hours total. Twice during the filtration, the filter was taken apart for cleaning and was conditioned with about 25 pounds of filter aid. During filtration, the product was at a temperature of about 90° C. or less. The final Ru content was less than 0.1 ppm.

Example 17

For each metathesized oil described in Example 7, about 20 grams of material was used. The oil was placed in a glass round bottom flask and a vacuum was applied (less than about 1 Torr) at room temperature. Once bubbling stopped, heat was applied to the oil according to the following temperature profile:

(1) The oil was heated from room temperature to 150° C. over 15 minutes. The oil was held at 150° C. for 15 minutes.

(2) The oil was heated from 150° C. to 200° C. over 15 minutes. The oil was held at 200° C. for 15 minutes.

(3) The oil was heated from 200° C. to 250° C. over 15 minutes. The oil was held at 250° C. for 15 minutes.

Throughout the distillation the volatiles collected were condensed and collected for GC analysis. The remaining material in the flask that did not distill out (i.e., residue) was retained for GPC analysis. The distillation results are shown in Table 10.

TABLE 10

| | Distillation Results | | | |
|---|---|---|---|---|
| Metathesized Oil Used (g) | Mass of volatiles collected (g) | Mass of residue (g) | Wt. % of volatiles | Wt. % of residue |
| Canola (21.4) | 3.2 | 17.1 | 15 | 81 |
| Castor (20.7) | 4.2 | 15.8 | 20 | 76 |
| Fish (20.7) | 2.8 | 17.4 | 14 | 84 |
| Linseed (21.3) | 2.8 | 18.1 | 13 | 85 |
| Palm (20.9) | 1.7 | 18.9 | 8 | 90 |

TABLE 10-continued

| | Distillation Results | | | |
|---|---|---|---|---|
| Metathesized Oil Used (g) | Mass of volatiles collected (g) | Mass of residue (g) | Wt. % of volatiles | Wt. % of residue |
| Soybean (21.6) | 2.9 | 18.3 | 13 | 85 |
| Sunflower (21.5) | 3.2 | 17.9 | 15 | 83 |
| High Oleic Sunflower (21.4) | 3.9 | 17.1 | 18 | 80 |
| Tallow (21.1) | 1.7 | 18.9 | 8 | 90 |

The fatty acid composition of certain vegetable oils is shown in Table 11 and the composition of the hydrogenated metathesis products (after stripping) made from the oils is shown in Table 12. As shown in the data, a relatively small change in saturated fatty acid content leads to a distinctly different polymer profile in the hydrogenated metathesis products. For example, soybean oil typically contains about 16 wt. % saturates (predominantly lauric and stearic fatty acids). As shown in Table 12, hydrogenated and metathesized soybean oil has a content of higher oligomers (i.e., pentamers and higher) of 18 wt. %. By comparison, canola oil and linseed oil have 7 wt. % and 10 wt. % saturates, respectively, and generate hydrogenated metathesized products having 43 wt. % and 41 wt. % higher oligomers (i.e., pentamers and higher).

As shown in the data, a relatively small change in saturates content of the starting oil results in more than double the amount of higher oligomers in the hydrogenated metathesized oil. Linseed and canola demonstrate another unexpected result in that the presence of polyunsaturates and monounsaturates appears to have little impact on the oligomer distribution.

TABLE 11

| | Fatty acid composition and IV typical of the reagent oils | | | | |
|---|---|---|---|---|---|
| Sample | Percent Saturates | Percent Mono-unsaturated Fatty Acids | Percent Poly-unsaturated Fatty Acids | Percent Hydroxy Fatty Acid | Iodine Value |
| Soybean | 16% | 24% | 61% | 0% | 133 |
| Canola | 7% | 65% | 28% | 0% | 113 |
| Castor | | | | 95% | |
| Linseed | 10% | 20% | 69% | 0% | 186 |
| Palm | 51% | 39% | 10% | 0% | 50 |
| Tallow | 54% | 43% | 3% | 0% | 44 |

TABLE 12

Gel permeation chromatography analysis of stripped, hydrogenated, and metathesized oils.

| Sample | ~280 g/mole (Fatty Acids and Hydrocarbons) | ~340 g/mole (Monoglyceride) | ~600 g/mole (Diglyceride) | ~800 g/mole (Triacylglyceride and Monomer) | ~1200 g/mole (Dimer) | ~2000 g/mole (Trimer) | ~2600 g/mole (Tetramer) | ~3200 g/mole (Pentamer) | ~3800 g/mole (Hexamer) |
|---|---|---|---|---|---|---|---|---|---|
| Soybean | 2% | 0.40% | 1% | 32% | 23% | 17% | 7% | 18% | — |
| Canola | 0.30% | 1% | 0.80% | 17% | 14% | 12% | 6% | 43% | 5% |
| Castor | 0.50% | 0.50% | 1.60% | 15% | 12% | 11% | 43% | 17% | — |
| Fish | 0.10% | 0.70% | — | 30% | 20% | 17% | 10% | 22% | — |
| Linseed | 0.40% | 0.30% | 0.80% | 19% | 14% | 12% | 8% | 41% | 4% |
| Palm | 0.20% | 0.60% | 3% | 45% | 27% | 15% | 4% | 4% | — |
| Tallow | — | 0.70% | 0.60% | 44% | 25% | 17% | 5% | 8% | — |

Example 18

Soybean Oil (Cargill RBD oil, 155.8 g, 0.177 mol) was purged with argon for 1 hr to remove oxygen. The ruthenium metathesis catalyst 827 (1.5 mg of catalyst, 10 ppm, on a mol/mol basis) was added to the soybean oil. The mixture was stirred at 70° C. for 2 hr and was cooled to room temperature. The percent conversion was determined from GC-analysis on the methanolysis products of the metathesized soybean oil.

The methanolysis products were prepared by heating a sample of the oil (~100 uL) in methanol (~0.5 mL) at 70° C. for 30 min in the presence of catalytic amount of sodium methoxide (NaOCH$_3$, 25 wt. % in methanol, ~5 uL). The GC conditions were as follows: column: HP-5™ (30 m×0.25 mmID, 0.25 um film thickness); 100° C. for 1 min, 10° C./min to 250° C., hold for 12 min.: Rt 12.6 min (Methyl Palmitate), Rt 14.2~14.5 min (Methyl Linolenate, Methyl Linoleate, and Methyl Oleate), Rt 14.7 min (Methyl Stearate).

Percent conversion was calculated from the GC chromatogram as 100% minus the sum of Methyl Palmitate, Methyl Linolenate (cis and trans isomers), Methyl Linoleate (cis and trans isomers), Methyl Oleate (cis and trans isomers) and Methyl Stearate. Percent conversion is reported in Table 13.

TABLE 13

Percent Conversion as a Function of Catalyst Loading
Catalyst Loading

| Soybean Oil Source | 50 ppm | 40 ppm | 35 ppm | 30 ppm | 20 ppm | 10 ppm |
|---|---|---|---|---|---|---|
| A | 63, 61 | | | | | |
| A | 67 | 65, 67 | 59, 67[1] | 37, 52[1] | | |
| A | 68 | 68 | | 48 | 32 | 15 |
| A | 69 | 69 | | 66 | 51 | 28 |
| A | 70 | 63 | | 38 | 31 | 7 |
| A | 68 | 66 | | 11[4] | 29 | |
| B | 60, 14[4] | 38, 31[4] | | | | |
| C | 51 | 49 | | | | |
| C (citric acid) | 68 | 68 | | 63, 68[1], 49[6], 49[7], 45[6,8], 60[7,8] | 61, 62[1] | 36 |
| C (no citric acid) | 67 | 66 | | 61 | 52 | |
| D (citric acid) | 71 | 70 | | 65 | | 23 |
| D (no citric acid) | 71 | 70, 69[9] | | 66, 67[9] | 60 | 44, 40[9] (12[9,10]) |

[1]Filtered through clay (5 wt %) before metathesis reaction.
[2]The conversion dropped dramatically after ~2 months storage period.
[3]The oil leaked from its container when received.
[4]The conversion dropped rapidly during time of storage.
[5]High conversions were obtained from well-packed oil.
[6]The oil was stored for 26 days from 1st experiment (once opened).
[7]The oil was stored for 28 days from receiving date (unopened).
[8]A new lot of metathesis catalyst was used for screening.
[9]827 was added as diluted-stock solution in DCM. The oil was stored for 42 days from 1st experiment (once opened).
[10]5 ppm of 827 was added.

ILLUSTRATIVE EMBODIMENTS

One embodiment is a wax for use as a candle and/or a candle comprising a wax comprising a metathesis product.

Another embodiment is a wax for use as a candle and/or a candle comprising a wax comprising a dibasic-acid-polyol oligomer.

Another embodiment is a wax for use as a candle and/or a candle comprising a wax having an acid profile comprising at least one dibasic acid.

Another embodiment is a wax for use as a candle and/or a candle comprising a wax having an acid profile comprising at least one of a C9 and a C15 acid. The acid profile may comprise both a C9 and a C15 acid. The C9 and/or C15 acid may be straight chained. Also, the C9 or C15 acid may be saturated, may be monounsaturated, or may include some other degree of unsaturation.

Another embodiment is a wax for use as a candle and/or a candle comprising a hydrogenated metathesis product formed from a base stock including polyol fatty acid ester having a fatty acid composition which includes at least one unsaturated fatty acid, and at least one of polyol fatty acid ester-based stock, paraffin wax, fatty acid, carnuba wax, and beeswax.

Another embodiment is a wax for use as a candle and/or a candle comprising a hydrogenated metathesis product formed from a base stock including polyol fatty acid ester having a fatty acid composition which includes at least one unsaturated fatty acid, polyol fatty acid ester stock, and paraffin wax. The wax has a melting point of about 55° C. to 70° C. The hydrogenated metathesis product is commonly formed from a vegetable oil base stock.

Another embodiment provides a candle wax which includes a hydrogenated metathesis product formed from a base stock including polyol fatty acid ester having a fatty acid composition which includes at least one unsaturated fatty acid. The wax also includes at least one of a polyol fatty acid ester stock, a paraffin wax, a fatty acid, and a natural wax, such as carnauba wax and/or beeswax. The candle wax commonly has a melting point of about 20° C. to 70° C. or about 45° C. to 70° C. and, where the wax is designed for use to form an extruded or pressed candle, a melting point of about 55° C. to 65° C. Typically, the wax has a fatty acid composition which includes 15:0 fatty acid and a linear terminal alkanedioic acid, such as a dioic acid having 18, 21 and/or 24 carbon atoms.

Commonly, the candle wax includes a metathesis product, such as a hydrogenated triacylglyceride ("TAG") metathesis oligomer. The metathesis product may be formed from a base stock which includes a vegetable oil having an Iodine Value of at least about 45. The hydrogenated metathesis product can include hydrogenated TAG metathesis dimer. In other embodiments, the hydrogenated metathesis product includes hydrogenated TAG metathesis tetramer. As employed herein, the terms "TAG metathesis oligomer," "TAG metathesis dimer" and "TAG metathesis tetramer" refer to oligomers, dimers and tetramers, respectively, formed from a metathesis reaction of one or more triacylglycerides. In many instances, the hydrogenated metathesis product may also include saturated C15-C24 hydrocarbon(s) that are hydrogenation products of unsaturated C15-C24 hydrocarbon(s). The present waxes of contain about 10 to 40 wt. % of the hydrogenated metathesis product.

In many instances, the candle wax can include additional wax-like material. For example, the wax may include a fatty acid, particularly a saturated fatty acid, such as stearic acid, palmitic acid or a mixture thereof. Other possible ingredients may include a monoglycerol ester, such as glycerol monostearate, glycerol monopalmitate or a mixture thereof. Other possible wax materials which may be suitably included in the present wax compositions include petroleum waxes, such as paraffin wax, natural waxes, such as carnauba wax and/or beeswax, or a mixture of such wax materials. Very commonly the candle wax includes hydrogenated polyol fatty acid ester stock, e.g., a fully hydrogenated soybean oil.

Other embodiments are directed to a wax which includes a hydrogenated metathesis product formed from a base stock including polyol fatty acid ester having a fatty acid composition which includes at least one unsaturated fatty acid; a polyol fatty acid ester stock; and a paraffin wax. Such waxes typically have a melting point of about 55° C. to 70° C. For example, such a wax may include about 10 to 30 wt. % of the hydrogenated metathesis product; about 20 to 60 wt. % of the paraffin wax; and about 20 to 50 wt. % of a triacylglyceride stock having an Iodine Value of about 70 or less.

Metathesis product based waxes having a melting point of about 45° C. to 75° C. may be particularly advantageous for use in forming candles. Wax compositions of this type having a somewhat higher melting point, e.g., about 55° C. to 75° C. and, more commonly about 60° C. to 70° C. can be particularly desirable for use in forming votive and pillar candles. Metathesis product based waxes having a somewhat softer texture and/or lower melting point (e.g., about 45° C. to 60° C. and, more commonly about 50° C. to 55° C.) can be particularly suitable for forming container candles.

The present metathesis product based waxes often have dibasic acid subunits which are derived from alpha,omega-dibasic acids, such octadecanedioic acid and/or corresponding alkanedioic acids having 21 or 24 carbon atoms. Further still, in some of these embodiments the acid profile may comprise about 15 to 20 wt. % dibasic acid(s) or more. The dibasic acid may include terminal carboxylic acid groups (e.g. $HO_2C-(CH_2)_{16}-CO_2H$). In some embodiments, linear terminal C18, C21, and/or C24 diacids may be the predominate types of dibasic acids present. A mixture of the dibasic acids and fatty acids, e.g., stearic acid, palmitic acid and/or a 15:0 fatty acid, are commonly esterified with glycerol to form a mixture which includes TAGs, TAG dimers, TAG trimers and TAG tetramers.

A candle formed from the above mentioned waxes would typically include a wick in addition to the wax.

A candle (A) comprising a wick; and a wax, which includes a metathesis product. The candle of embodiment A, wherein the metathesis product comprises a polyol-ester-based metathesis product. The candle of embodiment A, wherein the metathesis product comprises a fatty oil-based metathesis product, where the fatty oil-based metathesis product may comprise a fatty oil-based self-metathesis product. The candle of embodiment A, wherein the metathesis product comprises a polyol fatty acid based metathesis product. The candle of embodiment A, wherein the metathesis product comprises dibasic-acid polyol oligomers, which may include at least one of a dimer, a trimer, and a tetramer. Such dibasic-acid polyol oligomers may comprise more tetramers and/or higher oligomers than dimers or trimers. The candle of embodiment A, wherein the metathesis product has a fatty acid profile comprising dibasic acid(s), which may comprise more saturated dibasic acids than unsaturated dibasic acids. Such dibasic acids can comprise more C18 dibasic acids than dibasic acids having other lengths. The dibasic acids may consist essentially of straight-chained dibasic acids. The candle of embodiment A, wherein the wax has a melting point of about 45° C. to about 70° C. The candle of embodiment A, wherein the wax has an Iodine Value of no more than about 50 and, commonly, no more than about 20. The candle of embodiment A, wherein the wax further comprises petroleum wax. The candle of embodiment A, wherein the wax further comprises natural wax. The candle of embodiment A, wherein the candle wax has a fatty acid composition which includes 15:0 fatty acid.

The candle of embodiment A, wherein the candle wax includes at least one of polyol fatty acid ester stock, paraffin wax, fatty acid, carnuba wax and beeswax. The candle of embodiment A, wherein the candle wax includes polyol fatty acid ester stock, such as partially and/or fully hydrogenated triacylglyceride stock (e.g., partially and/or fully hydrogenated vegetable oil. The candle of embodiment A, wherein the candle wax includes paraffin wax. The candle of embodiment A, wherein the candle wax includes fatty acid, such as stearic acid and/or palmitic acid. The candle of embodiment A, wherein the candle wax includes carnauba wax and/or beeswax. The candle of embodiment A, wherein the candle wax includes polyol fatty acid ester stock, which may comprise glycerol monostearate, glycerol monopalmitate or a mixture thereof.

A candle (B) comprising a wick; and a wax comprising dibasic-acid-polyol oligomers. The polyol of such oligomers comprises glycerol and, in some instances may consist essentially of glycerol. The candle of embodiment B, wherein the dibasic-acid polyol oligomers comprise at least one of a dimer, a trimer, and a tetramer. Such dibasic-acid polyol oligomers may comprise more tetramers than dimers or trimers. In some instances, at least about half of the dibasic acid of the oligomers may be comprised of esters of dibasic acids having at least 18 carbons. The candle of embodiment B, wherein the wax has a acid profile comprising dibasic acids.

The candle of embodiment B, wherein the candle wax has a fatty acid composition which includes 15:0 fatty acid.

The candle of embodiment B, wherein the candle wax includes at least one of polyol fatty acid ester stock, paraffin wax, fatty acid, carnuba wax and beeswax. The candle of embodiment B, wherein the candle wax includes polyol fatty acid ester stock, such as partially and/or fully hydrogenated triacylglyceride stock (e.g., partially and/or fully hydrogenated vegetable oil. The candle of embodiment B, wherein the candle wax includes paraffin wax. The candle of embodiment B, wherein the candle wax includes fatty acid, such as stearic acid and/or palmitic acid. The candle of embodiment B, wherein the candle wax includes carnauba wax and/or beeswax. The candle of embodiment B, wherein the candle wax includes polyol fatty acid ester stock, which may comprise glycerol monostearate, glycerol monopalmitate or a mixture thereof.

A candle (C) comprising a wick; and a wax having an acid profile comprising dibasic acids. Such a wax may have an acid profile wherein the dibasic acids comprise more saturated dibasic acids than unsaturated dibasic acids. The candle of embodiment C, wherein the dibasic acids comprise more C18 dibasic acids than other length dibasic acids. The candle of embodiment C, wherein the wax comprises dibasic-acid-polyol oligomers. The candle of embodiment C, wherein the candle wax has a fatty acid composition which includes 15:0 fatty acid.

The candle of embodiment C, wherein the candle wax includes at least one of polyol fatty acid ester stock, paraffin wax, fatty acid, carnauba wax and beeswax. The candle of embodiment C, wherein the candle wax includes polyol fatty acid ester stock, such as partially and/or fully hydrogenated triacylglyceride stock (e.g., partially and/or fully hydrogenated vegetable oil. The candle of embodiment C, wherein the candle wax includes paraffin wax. The candle of embodiment C, wherein the candle wax includes fatty acid, such as stearic acid and/or palmitic acid. The candle of embodiment C, wherein the candle wax includes carnauba wax and/or beeswax. The candle of embodiment C, wherein the candle wax includes polyol fatty acid ester stock, which may comprise glycerol monostearate, glycerol monopalmitate or a mixture thereof.

A candle D comprising a wick; and a wax, wherein the wax comprises a metathesis product derived from a base stock comprising triacylglyceride. The wax commonly has a melting point of about 45° C. to about 70° C. The metathesis product typically includes oligomers comprising glycerol subunits; and has an acid profile including one or more alpha, omega-dibasic acids. The wax can have a fatty acid composition which includes 15:0 fatty acid.

The candle of embodiment D, wherein the candle wax includes at least one of polyol fatty acid ester stock, paraffin wax, fatty acid, carnauba wax and beeswax. The candle of embodiment D, wherein the candle wax includes polyol fatty acid ester stock, such as partially and/or fully hydrogenated triacylglyceride stock (e.g., partially and/or fully hydrogenated vegetable oil. The candle of embodiment D, wherein the candle wax includes paraffin wax. The candle of embodiment D, wherein the candle wax includes fatty acid, such as stearic acid and/or palmitic acid. The candle of embodiment D, wherein the candle wax includes carnauba wax and/or beeswax. The candle of embodiment D, wherein the candle wax includes polyol fatty acid ester stock, which may comprise glycerol monostearate, glycerol monopalmitate or a mixture thereof.

A candle wax (E) comprising a hydrogenated metathesis product formed from a base stock including polyol fatty acid ester having a fatty acid composition which includes at least one unsaturated fatty acid; and at least one of polyol fatty acid ester stock, petroleum wax, fatty acid, carnauba wax and beeswax. The wax of embodiment E, wherein the candle wax has a melting point of about 45° C. to 70° C. and, commonly, about 55° C. to 65° C. The wax of embodiment E, wherein the candle wax has a fatty acid composition which includes 15:0 fatty acid. The wax of embodiment E, wherein the hydrogenated metathesis product comprises hydrogenated TAG metathesis oligomer. The wax of embodiment E, wherein the hydrogenated metathesis product comprises hydrogenated TAG metathesis dimer. The wax of embodiment E, wherein the hydrogenated metathesis product comprises hydrogenated TAG metathesis tetramer. The wax of embodiment E, wherein the hydrogenated metathesis product comprises saturated C15-C24 hydrocarbon. The wax of embodiment E, wherein the base stock includes a vegetable oil having an Iodine Value of at least about 50 and, in some instances, no more than about 20. The wax of embodiment E, wherein the candle wax has an Iodine Value of no more than about 50 and, in some instances, no more than about 20. The wax of embodiment E, wherein the candle wax contains about 10 to 40 wt. % of the hydrogenated metathesis product.

The candle wax of embodiment E comprising stearic acid and/or palmitic acid. The candle wax of embodiment E, wherein the wax comprises glycerol monostearate, glycerol monopalmitate or a mixture thereof. The candle wax of embodiment E, wherein wax comprises paraffin wax. The candle wax of embodiment E, wherein the wax comprises carnauba wax, beeswax or a mixture thereof. The candle wax of embodiment E, wherein the wax comprises hydrogenated polyol fatty acid ester stock. The candle wax of embodiment E, wherein the wax includes polyol fatty acid ester stock, such as partially and/or fully hydrogenated triacylglyceride stock (e.g., partially and/or fully hydrogenated vegetable oil). The candle wax of embodiment E, wherein the wax includes paraffin wax. The candle wax of embodiment E, wherein the wax includes fatty acid, which includes stearic acid and/or palmitic acid. The candle wax of embodiment E, wherein the wax includes polyol fatty acid ester stock, which may comprise glycerol monostearate, glycerol monopalmitate or a mixture thereof.

A wax (F) comprising:
a hydrogenated metathesis product formed from a base stock including polyol fatty acid ester having a fatty acid composition which includes at least one unsaturated fatty acid;
polyol fatty acid ester stock; and
paraffin wax;
wherein the wax has a melting point of about 55° C. to 70° C.

The wax of embodiment F, comprising about 10 to 30 wt. % of the hydrogenated metathesis product; about 20 to 60 wt. % of the paraffin wax; and about 20 to 50 wt. % of a triacylglyceride stock having an Iodine Value of about 0 to 70. The wax of embodiment F, wherein the wax has a fatty acid composition which includes 15:0 fatty acid.

The wax of embodiment F further comprising stearic acid and/or palmitic acid. The wax of embodiment F, wherein the wax further comprises glycerol monostearate, glycerol monopalmitate or a mixture thereof. The wax of embodiment F, wherein the wax further comprises carnauba wax, beeswax or a mixture thereof. The wax of embodiment F, wherein the wax further comprises hydrogenated polyol fatty acid ester stock. The wax of embodiment F, wherein the wax further includes polyol fatty acid ester stock, such as partially and/or fully hydrogenated triacylglyceride stock (e.g., partially and/ or fully hydrogenated vegetable oil). The wax of embodiment F, wherein the wax further comprises paraffin wax. The wax of embodiment F, wherein the wax further comprises fatty acid, which includes stearic acid and/or palmitic acid. The wax of embodiment F, wherein the wax further comprises polyol fatty acid ester stock, which may comprise glycerol monostearate, glycerol monopalmitate or a mixture thereof.

For certain applications, e.g., where it may be desirable to produce the candle via extrusion molding techniques, wax may have a fatty acid composition which includes 18:2 fatty acid (e.g., about 1 to 10 wt. % 18:2 fatty acid). Such a wax may have a relatively low Iodine Value, e.g., no more than about 25 and may include paraffin wax. The fatty acid composition of such waxes commonly includes 15:0 fatty acid. Waxes with a melting point of about 140° F. to 150° F. (circa 60° C. to 65° C.) may be particularly suitable for compression molding.

For applications where it may be desirable to produce the candle via compression molding techniques, wax may have a fatty acid composition which includes a very low level of polyunsaturated fatty acids (e.g., no more than about 2 wt. % 18:2 fatty acid). The fatty acid composition of such waxes may include 15:0 fatty acid. Such a wax may have a relatively low Iodine Value, e.g., no more than about 20 and, more suitably no more than about 10, and may include paraffin wax. Waxes with a melting point of about 140° F. to 150° F. (circa 60° C. to 65° C.) may be particularly suitable for compression molding. Suitable examples include wax blends which include 10 to 30 wt. % hydrogenated metathesis product (e.g., hydrogenated metathesis product formed from a vegetable oil, such soybean and/or cottonseed oil), 20 to 50 wt. % of a triacylglyceride stock having an Iodine Value of no more than about 25 (e.g., a hydrogenated vegetable oil) and about 20 to 60 wt. % paraffin wax (e.g., a paraffin wax having a melting point of about 145° F. to 150° F.).

Certain embodiments of the present wax compositions may be used a base waxes, which can be blended with other wax(es) and additives to form wax blends suitable for use as a candle wax. For example, wax compositions having a melting point of at least about 55° C., an Iodine Value of no more than about 60, and including at least about 50 wt. % triacylglyceride stock and metathesized triacylglyceride stock, can be used employed as such a base wax composition. Where the candle wax is designed to be used for compression and/or extrusion molding processes, the base wax may desirably have a somewhat lower Iodine Value, e.g., no more than about 30 and more suitably, no more than about 15. Such base waxes may often have a melting point of about 55° C. to 65° C. and commonly at least about 58° C.

In another embodiment, the wax has a melting point of about 55° C. to 70° C. and an Iodine Value of no more than about 25; wherein the wax comprises at least about 10 wt. % TAG metathesis oligomers and at least about 50 wt. % triacylglyceride. The area ratio of (total TAG metathesis oligomers)/(TAG metathesis dimers) is commonly at least about 3:1.

In another embodiment, the wax has a melting point of about 55° C. to 70° C. and an Iodine Value of no more than about 25 and comprises triacylglyceride, TAG metathesis dimers, TAG metathesis trimers, and TAG metathesis tetramers and higher oligomers. Such a wax typically has a fatty acid composition which includes at least about 50 wt. % 18:0 fatty acid. The wax also generally includes more, based on area %, of TAG metathesis tetramers and higher oligomers than TAG metathesis dimers. Such a wax may include about 10 to 30 wt. % of TAG metathesis oligomers and about 60 to 90 wt. % of the triacylglyceride. Waxes of this type may desirably have a relatively low Iodine Value, e.g., no more than about 20 and for some applications an Iodine Value of no more than about 10. Where the wax is designed to be used in a compression molding process, its fatty acid composition may include no more than about 2 wt. % 18:2 fatty acid.

Another embodiment of the present wax has a melting point of about 50° C. to 70° C. and an Iodine Value of no more than about 75 and comprises triacylglyceride, TAG metathesis dimers, TAG metathesis trimers, and TAG metathesis tetramers and higher oligomers. Such a wax may include, based on area %, more TAG metathesis tetramers and higher oligomers than TAG metathesis dimers; The wax can have a fatty acid composition which includes at least about 50 wt. % 18:0 fatty acid and, for some applications, it may desirable to employ a wax which has a fatty acid composition which includes about 60 wt. % or more 18:0 fatty acid. The fatty acid composition of such waxes may include about 5 to 15 wt. % 16:0 fatty acid.

Yet another embodiment provides a wax having a fatty acid composition which includes at least about 2 wt. % 15:0 fatty acid; at least about 50 wt. % 18:0 fatty acid; no more than about 2 wt. % 18:2 fatty acid; and at least about 10 wt. % alpha,omega-dibasic acid having 18 to 24 carbon atoms. Waxes of this type may suitably have has an Iodine Value of no more than about 15 and a melting point of about 55° C. to 65° C. Such a wax typically includes about 10 to 30 wt. % TAG metathesis oligomers and at least about 60 wt. % triacylglyceride.

The invention has been described with reference to various specific and illustrative embodiments and techniques. However, it should be understood that many variations and modifications may be made while remaining within the spirit and scope of the invention.

What is claimed is:

1. A wax composition comprising:
    (a) a metathesis product formed from a base stock comprising a polyol fatty acid ester having a fatty acid composition that includes at least one unsaturated fatty acid; and
    (b) at least one of: polyol fatty acid ester stock, paraffin wax, fatty acid, carnauba wax, and beeswax;
    wherein the wax composition has a melting point of about 20° C. to about 70° C.

2. The wax of claim 1, wherein the wax composition has a melting point of about 45° C. to about 70° C.

3. The wax of claim 1, wherein the metathesis product is hydrogenated.

4. The wax of claim 1, wherein the metathesis product comprises hydrogenated triacylglyceride metathesis product.

5. The wax of claim 1, wherein the base stock comprises a vegetable oil having an Iodine Value of at least about 45.

6. The wax of claim 1, wherein the base stock comprises soybean oil, canola oil, palm oil, sunflower oil, cottonseed oil, rapeseed oil, tallow, linseed oil, corn oil, palm kernel oil, coconut oil, lard, chicken fat, or tall oil.

7. The wax of claim 1, wherein the wax comprises about 10 to 40 wt. % of the metathesis product.

8. The wax of claim 1, wherein the wax comprises stearic acid, palmitic acid or a mixture thereof.

9. The wax of claim 1, wherein the wax comprises glycerol monostearate, glycerol monopalmitate or a mixture thereof.

10. A wax composition comprising:
a hydrogenated metathesis product formed from a base stock comprising polyol fatty acid ester having a fatty acid composition that includes at least one unsaturated fatty acid;
a polyol fatty acid ester stock; and
a paraffin wax;
wherein the wax composition has a melting point of about 45° C. to about 70° C.

11. The wax composition of claim 10, comprising:
about 10 to 30 wt. % of the hydrogenated metathesis product;
about 20 to 50 wt. % of a triacylglycerol stock having an Iodine Value of no more than about 70; and
about 20 to 60 wt. % of the paraffin wax.

12. A candle comprising:
a wick; and
a wax comprising a metathesis product.

13. The candle of claim 12, wherein the metathesis product is derived from a base stock comprising a triacylglyceride.

14. The candle of claim 12, wherein the wax has a melting point of about 45° C. to about 70° C.

15. The candle of claim 12, wherein the base stock is a vegetable oil selected from the group consisting of soybean oil, canola oil, palm oil, sunflower oil, cottonseed oil, rapeseed oil, linseed oil, corn oil, palm kernel oil, coconut oil, or tall oil.

16. The candle of claim 12, wherein the metathesis product is hydrogenated.

17. The candle of claim 12, wherein the candle further includes a fragrance present in an amount up to about 15 wt. %.

18. The candle of claim 12, wherein the candle is made by compression molding and comprises about 1.5 wt. % or greater fragrance.

19. The candle of claim 12, wherein the candle is made by extrusion and comprises up to about 3 wt. % or greater fragrance.

20. The candle of claim 12, wherein the wax comprises:
a hydrogenated metathesis product formed from a base stock comprising polyol fatty acid ester having a fatty acid composition that includes at least one unsaturated fatty acid;
a polyol fatty acid ester stock; and
a paraffin wax;
wherein the wax has a melting point of about 45° C. to about 70° C.

* * * * *